United States Patent [19]

Taylor

[11] 4,235,619

[45] Nov. 25, 1980

[54] METHOD OF CONTROLLING AQUATIC WEEDS AND ALGAE

[75] Inventor: Harold M. Taylor, Indianapolis, Ind.

[73] Assignee: Eli Lilly and Company, Indianapolis, Ind.

[21] Appl. No.: 21,670

[22] Filed: Mar. 19, 1979

Related U.S. Application Data

[63] Continuation-in-part of Ser. No. 810,219, Jun. 27, 1977, Pat. No. 4,152,136, which is a continuation-in-part of Ser. No. 591,661, Jul. 3, 1975, abandoned, which is a continuation-in-part of Ser. No. 501,424, Aug. 28, 1974, abandoned.

[51] Int. Cl.$^3$ .............................................. A01N 43/40
[52] U.S. Cl. ............................................ 71/66; 71/67
[58] Field of Search ...................................... 71/66, 67

[56] References Cited

U.S. PATENT DOCUMENTS

| | | | |
|---|---|---|---|
| 3,244,722 | 4/1966 | Johnston et al. | 71/66 |
| 4,116,665 | 9/1978 | Krumkalns | 71/66 |

OTHER PUBLICATIONS

Parra et al., Proc. Ewrs. 5th Symp. on Aquatic Weeds-9/1978.
Arnold-Fluridone-A New Aquatic Herbicide Presented at Aquatic Plant Management Society-Jacksonville, Fla.-7/1978.
Berard et al., Weed Sci. Soc. of Am. Abstracts, vol. 28 (1977), p. 13.
Waldrep et al., J. Agri. Food Chem., vol. 24, (1976), 1250-1251.
Waldrep et al-Weed. Sci. Soc. of Am. Abstracts-vol. 226 (1977), p. 109.
Webster, Proc. Southern Weed Sci. Soc., vol. 30 (1977), pp. 103-112.
Wills, Proc. Southern Weed Sci. Soc. (1977), vol. 30, 113-118.
Waldrep et al., Proc. Southern Weed Sci. Soc., vol. 30 (1977), p. 401.
Deehoretz et al., Proc. West. Soc. Weed Sci., vol. 31 (1978), pp. 111-116.
McGowan et al., "A New Herbicide for Aquatic Plant Management".
Sanders et al., Evaluation of Two Autumn Applied Fluoridone Formulations for the Control of Hydrilla in Gatunwake, Panama Canal Zone.

*Primary Examiner*—Catherine L. Mills
*Attorney, Agent, or Firm*—Joseph A. Jones; Arthur R. Whale

[57] ABSTRACT

A method of reducing the vigor of aquatic weeds and algae makes use of a class of 3-phenyl-4(1H)-pyridones and pyridinethiones. The new compounds are characterized by a methyl group on the nitrogen, and usually bear a 5-substituent chosen from a class which is described herein. The phenyl ring may be substituted. The compounds effectively control aquatic weeds and algae, and kill the plants slowly, so that their decomposition does not deplete oxygen in the treated body of water.

44 Claims, No Drawings

METHOD OF CONTROLLING AQUATIC WEEDS AND ALGAE

CROSS-REFERENCE

This application is a continuation-in-part of my copending application, Ser. No. 810,219, filed June 27, 1977, now U.S. Pat. No. 4,152,136 which is a continuation-in-part of my then copending application, Ser. No. 591,661, filed July 3, 1975, now abandoned, which is a continuation-in-part of my then copending application, Ser. No. 501,424, filed Aug. 28, 1974, now abandoned.

BACKGROUND OF THE INVENTION

This invention belongs to the field of agricultural chemistry, and provides to the art a new method of controlling aquatic weeds and algae. The safe control of aquatic weeds and algae has become more and more important. Such weeds and algae clog water-ways, plug up water-handling equipment, are often aesthetically unacceptable, and can become so lush that even fish populations are injured. In addition, many types of algae are toxic to mammals. Therefore, herbicides effective against aquatic weeds and algae are in demand and research on the subject has been going forward with vigor.

The compounds used in the method of this invention kill the plants slowly, so that their decomposition does not deplete oxygen in the treated body of water, and are quite safe to fish, phytoplankton and zooplankton.

Despite the great amount of research which has been performed in the field of agricultural chemistry, active compounds closely related to the compounds of the present invention have not been previously discovered. The polyhalopyridones, which have two or more chlorine atoms as well as other alkyl and halo substituents on the pyridine ring, are known herbicides, but are obviously quite distinct from the present invention.

The organic chemical art has explored the pyridones rather extensively. For example, Ishibe et al., *J. Am. Chem. Soc.* 95, 3396–3397 (1973), disclosed a rearrangement of 3,5-diphenyl-1,2,6-trimethyl-4(1H)-pyridone. Such compounds, however, are not herbicides. Leonard et al., *J. Am. Chem. Soc.* 77, 1852–1855 (1955), taught the synthesis of 3,5-dibenzyl-1-methyl-4(1H)-pyridones, which compounds also have no herbicidal activity. The same principal author also disclosed 3,5-di(substituted-benzylidene)tetrahydro-4-pyridones, *J. Am. Chem. Soc.* 79, 156–160 (1957).

Light et al., *J. Org. Chem.* 25, 538–546 (1960), taught a number of 4-pyridone compounds including 2,6-diphenyl-1-methyl-4(1H)-pyridone, and related compounds bearing phenyl-ring substituents, none of which are herbicidally active.

An interesting recent article was published by El-Kholy et al. in *J. Hetero. Chem.* 10, 665–667 (published Sept. 7, 1973). El-Kholy described a synthesis of 3,5-diphenyl-1-methyl-4(1H)-pyridone and related compounds by the reaction with methylamine of the sodium salt of 1,5-dihydroxy-2,4-diphenyl-1,4-pentadien-3-one.

A counterpart of the parent application, Ser. No. 591,661, has been patented as Belgian Pat. No. 832,702 (1976).

Articles and reports reporting the herbicidal use of compounds of this invention include the following:

Anonymous, Technical Report on Fluridone, Lilly Research Laboratories, Indianapolis, Indiana.

Berard and Rainey, *Weed Sci. Soc. of Am. Abstracts* 28, p. 13 (1977);

Parka, Fluridone: A New Herbicide for Use in Aquatic Weed Control Systems, Proceedings of the European Weed Research Society, Amsterdam, September 1978.

Waldrep and Taylor, *J. Agric. Food Chem.* 24, 1250–51 (1976);

Waldrep and Taylor, *Weed Sci. Soc. of Am. Abstracts* 266, p. 109 (1977);

Webster, *Proc. Southern Weed Sci. Soc.* 30, 103–12 (1977);

Wills, *Proc. Southern Weed Sci. Soc.* 30, 113–18 (1977).

SUMMARY OF THE INVENTION

A series of new 3-phenyl-4(1H)-pyridones(thiones) are herbicides which are active against aquatic weeds and algae. This invention provides a method of reducing the vigor of aquatic weeds or algae which comprises applying to water infested with or likely to be infested with such weeds or algae an herbicidally or algicidally effective amount of a compound of the formula

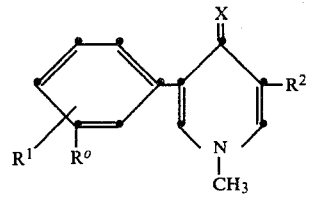

wherein
  X represents oxygen or sulfur;
  $R^o$ represents halo,
    $C_1$–$C_4$ alkyl,
    $C_1$–$C_4$ alkyl substituted with halo,
    $C_1$–$C_4$ alkyl monosubstituted with phenyl, cyano or $C_1$–$C_3$ alkoxy,
    $C_2$–$C_4$ alkenyl,
    $C_3$–$C_6$ cycloalkyl,
    $C_4$–$C_8$ cycloalkylalkyl,
    $C_1$–$C_3$ alkanoyloxy,
    phenyl,
    nitro,
    hydroxy,
    $C_1$–$C_3$ alkoxycarbonyl,
    —O—$R^3$,
    —S—$R^3$, or
    —SO—$R^3$;
  $R^3$ represents $C_1$–$C_4$ alkyl,
    $C_1$–$C_4$ alkyl substituted with halo,
    $C_1$–$C_4$ alkyl monosubstituted with phenyl, cyano or $C_1$–$C_3$ alkoxy,
    phenyl,
    phenyl monosubstituted with halo, $C_1$–$C_3$ alkyl, $C_1$–$C_3$ alkoxy or nitro,
    $C_3$–$C_6$ cycloalkyl,
    $C_4$–$C_8$ cycloalkylalkyl, or
    $C_2$–$C_4$ alkenyl;
  $R^1$ represents halo,
    hydrogen,
    $C_1$–$C_4$ alkyl,
    $C_1$–$C_4$ alkyl substituted with halo,
    $C_1$–$C_4$ alkyl monosubstituted with phenyl, cyano or $C_1$–$C_3$ alkoxy,
    methoxy, or
    $C_2$–$C_4$ alkenyl;

$R^2$ represents hydrogen,
$C_1$–$C_3$ alkoxycarbonyl,
$C_1$–$C_6$ alkyl,
$C_1$–$C_6$ alkyl substituted with halo or $C_1$–$C_3$ alkoxy,
$C_2$–$C_6$ alkenyl,
$C_2$–$C_6$ alkenyl substituted with halo or $C_1$–$C_3$ alkoxy,
$C_3$–$C_6$ cycloalkyl,
$C_3$–$C_6$ cycloalkyl substituted with halo, $C_1$–$C_3$ alkyl or $C_1$–$C_3$ alkoxy,
$C_4$–$C_6$ cycloalkenyl,
$C_4$–$C_8$ cycloalkylalkyl,
phenyl—$C_1$–$C_3$ alkyl,
—O—$R^4$,
—S—$R^4$,
—SO—$R^4$; or

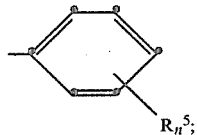

$R^4$ represents $C_1$–$C_3$ alkyl,
$C_1$–$C_3$ alkyl substituted with halo,
$C_2$–$C_3$ alkenyl,
$C_2$–$C_3$ alkenyl substituted with halo,
benzyl,
phenyl or
phenyl substituted with halo, $C_1$–$C_3$ alkyl or $C_1$–$C_3$ alkoxy;
the $R^5$ groups independently represent halo,
$C_1$–$C_4$ alkyl,
$C_1$–$C_4$ alkyl substituted with halo,
$C_1$–$C_4$ alkyl monosubstituted with phenyl, cyano or $C_1$–$C_3$ alkoxy,
$C_2$–$C_4$ alkenyl,
$C_3$–$C_6$ cycloalkyl,
$C_4$–$C_8$ cycloalkylalkyl,
$C_1$–$C_3$ alkanoyloxy,
hydroxy,
$C_1$–$C_3$ alkoxycarbonyl,
—O—$R^6$,
—S—$R^6$, or
—SO—$R^6$;
$R^6$ represents $C_1$–$C_4$ alkyl,
$C_1$–$C_4$ alkyl substituted with halo, or
$C_1$–$C_4$ alkyl monosubstituted with phenyl, cyano or $C_1$–$C_3$ alkoxy;
n represents 0–2; and the acid addition salts thereof.

A preferred group of compounds comprises those wherein $R^1$ represents hydrogen. Highly preferred compounds are those of the above group wherein $R^o$ represents trifluoromethyl.

A particularly preferred class of compounds are those of the formula

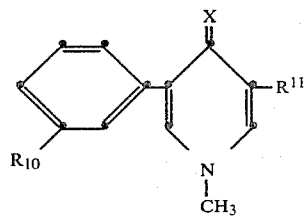

wherein

X represents oxygen or sulfur;
$R^{10}$ represents trifluoromethyl, $C_1$–$C_3$ alkyl, halo, methoxy or methylthio;
$R^{11}$ represents $C_1$–$C_4$ alkyl, $C_1$–$C_3$ alkoxy, $C_1$–$C_3$ alkylthio, phenyl, phenoxy, phenylthio, or phenyl, phenoxy or phenylthio monosubstituted with trifluoromethyl, $C_1$–$C_3$ alkyl, halo, methoxy or methylthio.

A further preferred group of compounds are of the formula

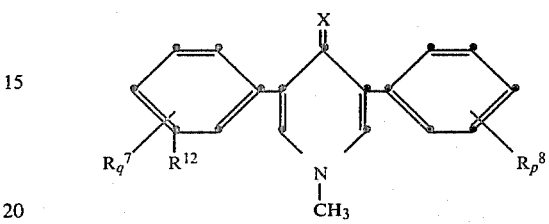

wherein
X represents oxygen or sulfur;
q represents 0–1;
p represents 0–2;
the $R^7$, $R^8$ and $R^{12}$ groups independently represent halo, $C_1$–$C_3$ alkyl, trifluoromethyl or $C_1$–$C_3$ alkoxy.

Within all of the above-described classes of compounds of this invention, the pyridones wherein X represents oxygen are a preferred subclass, and the pyridinethiones wherein X represents sulfur are another preferred subclass.

DESCRIPTION OF THE PREFERRED EMBODIMENT

In the above formula, the general chemical terms are used in their normal meanings. For example, the terms $C_1$–$C_3$ alkyl, $C_1$–$C_3$ alkoxy, $C_1$–$C_3$ alkylthio, $C_1$–$C_4$ alkyl, $C_2$–$C_4$ alkenyl, $C_1$–$C_6$ alkyl and $C_2$–$C_6$ alkenyl refer to such groups as methyl, ethyl, isopropyl, vinyl, allyl, methoxy, isopropoxy, methylthio, isopropylthio, isobutyl, hexyl, pentyl and crotyl.

The terms $C_3$–$C_6$ cycloalkyl and $C_4$–$C_6$ cycloalkenyl refer to such groups as cyclopropyl, cyclobutyl, cyclohexyl, cyclobutenyl, cyclopentenyl and cyclohexadienyl.

The term $C_4$–$C_8$ cycloalkylalkyl refers to such groups as cyclopropylmethyl, cyclobutylmethyl, cyclohexylmethyl and cyclohexylethyl.

The term $C_1$–$C_3$ alkanoyloxy refers to groups such as formyloxy, acetoxy and propionyloxy.

The term $C_1$–$C_3$ alkoxycarbonyl refers to groups such as methoxycarbonyl, ethoxycarbonyl and isopropoxycarbonyl.

The term halo refers to fluoro, chloro, bromo, and iodo.

The compounds described above can form acid addition salts, and such salts are useful embodiments of the invention. The preferred salts are the hydrohalides such as hydroiodides, hydrobromides, hydrochlorides and hydrofluorides. Salts of the sulfonic acids are also particularly desirable. Such salts include sulfonates, methylsulfonates and toluenesulfonates.

Although the above general description of the compounds is believed to describe them unambiguously, a group of exemplary compounds of the invention will be named below to assure that the invention is understood by those skilled in the art.

1-methyl-3,5-bis(3-methoxyphenyl)-4(1H)-pyridinethione
3-(3,5-diiodophenyl)-5-(3-propylphenyl)-1-methyl-4(1H)-pyridinethione
1-methyl-3-(3-chlorophenyl)-5-(2,3-diethoxyphenyl)-4(1H)-pyridinethione
3-(3,5-difluorophenyl)-1-methyl-5-phenyl-4(1H)-pyridone
1-methyl-3-(3,5-diethylphenyl)-5-(2,4-diethylphenyl)-4(1H)-pyridinethione
3-(2,6-difluorophenyl)-5-(3-iodophenyl)-1-methyl-4(1H)-pyridone
3-(3,5-dibromophenyl)-5-(3-isopropoxyphenyl)-1-methyl-4(1H)-pyridone
3-(2-iodophenyl)-5-(3-isopropylphenyl)-1-methyl-4(1H)-pyridinethione
3-(3-bromo-5-ethylphenyl)-5-(3-methylphenyl)-1-methyl-4(1H)-pyridinethione
1-methyl-3,5-bis(3-ethyl-4-methoxyphenyl)-4(1H)-pyridone
1-methyl-3-(3-methyl-5-propylphenyl)-5-phenyl-4(1H)-pyridinethione
3-(2-chloro-4-iodophenyl)-5-(3-fluorophenyl)-1-methyl-4(1H)-pyridinethione
3-(3-chlorophenyl)-5-[2,4-bis(trifluoromethyl)phenyl]-1-methyl-4(1H)-pyridone
3-benzylsulfinyl-1-methyl-5-(3-fluoro-5-propylphenyl)-4(1H)-pyridone
3-(3-chloromethylphenyl)-1-methyl-4(1H)-pyridone
3-(3-heptafluoropropylphenyl)-5-hexyl-1-methyl-4(1H)-pyridinethione
3-(3,5-diethylphenyl)-1-methyl-5-[3-(4,4-dibromobutyl)phenyl]-4(1H)-pyridone
3-(2,3-dipropylphenyl)-1-methyl-5-trifluoromethyl-4(1H)-pyridone
3-(3-benzylphenyl)-1-methyl-5-(2-fluoroethyl)-4(1H)-pyridone
3-(2-chloroethyl)-5-[3-(2,2-diiodobutyl)phenyl]-1-methyl-4(1H)-pyridinethione
3-(3-chloro-2-methoxyphenyl)-5-(1,1-dibromopropyl)-1-methyl-4(1H)-pyridone
3-(3-butylphenyl)-5-methoxymethyl-1-methyl-4(1H)-pyridone
1-methyl-3,5-bis(3-trifluoromethylphenyl)-4(1H)-pyridinethione
3-(3-hexenyl)-5-[3-(2-methoxyethyl)phenyl]-1-methyl-4(1H)-pyridinethione
3-(2,2-dichlorovinyl)-1-methyl-5-[3-(3-propoxypropyl)phenyl]-4(1H)-pyridone
3-(2-bromo-1-butenyl)-5-[3-(2-ethoxybutyl)phenyl]-1-methyl-4(1H)-pyridone
3-(2-iodo-1-hexenyl)-1-methyl-5-(3-vinylphenyl)-4(1H)-pyridinethione
3-(3-allylphenyl)-1-methyl-5-phenyl-4(1H)-pyridinethione
3-(2-methoxyallyl)-1-methyl-5-(3-trifluoromethylphenyl)-4(1H)-pyridinethione
3-(4-ethoxy-2-pentenyl)-5-[3-(1,3-butadienyl)phenyl]-1-methyl-4(1H)-pyridone
1-methyl-3-[3-(3-butenyl)phenyl]-5-phenyl-4(1H)-pyridone, methanesulfonate
3-(2-ethyl-3-fluorophenyl)-5-vinyl-1-methyl-4(1H)-pyridinethione
3-[3-(2,4-dibromo-2-butenyl)phenyl]-1,5-dimethyl-4(1H)-pyridone
3-(2-hexenyl)-1-methyl-5-[3-(1,1,2,2-tetrachloro-3-butenyl)phenyl]-4(1H)-pyridone
3-cyclopropyl-5-[3-(2-fluoro-1-propenyl)phenyl]-1-methoxy-4(1H)-pyridinethione
1-methyl-3-(2-propoxyethyl)-5-phenyl-4(1H)-pyridinethione, hydrofluoride
3-(6-ethoxyhexyl)-5-(3-ethyl-5-iodophenyl)-1-methyl-4(1H)-pyridone
3-[3-(2-cyanoethyl)phenyl]-1-methyl-5-(2-pentenyl)-4(1H)-pyridone
3-cyclobutyl-5-[3-(2-iodovinyl)phenyl]-1-methyl-4(1H)-pyridone
1-methyl-3-(2-chlorocyclopropyl)-5-[3-(3-chloropropyl)phenyl]-4(1H)-pyridone
3-[3-(1,1-dibromo-3-butenyl)phenyl]-1-methyl-5-(2-methylcyclobutyl)-4(1H)-pyridone
3-[3-(2-propenyl)phenyl]-5-(2-methoxycyclopropyl)-1-methyl-4(1H)-pyridinethione
3-(3-cyclopropylphenyl)-1-methyl-5-(2-propoxycyclobutyl)-4(1H)-pyridinethione
3-(2-cyclobutenyl)-5-(3-cyclopentylphenyl)-1-methyl-4(1H)-pyridinethione
3-(3-cyclohexenyl)-5-(3-cyclohexylphenyl)-1-methyl-4(1H)-pyridone
3-[3-(1-cyclobutenyl)phenyl]-5-methoxy-1-methyl-4(1H)-pyridone, toluenesulfonate
3-chloromethoxy-1-methyl-5-(3-formyloxyphenyl)-4(1H)-pyridinethione
1-methyl-3-(3-propionyloxyphenyl)-5-trifluoromethoxy-4(1H)-pyridinethione
3-[3-(2-cyclohexenyl)phenyl]-5-isopropoxy-1-methyl-4(1H)-pyridone
3-(3-biphenylyl)-1-methyl-5-vinyloxy-4(1H)-pyridinethione
3-(2,2-dichlorovinyloxy)-5-(3-biphenylyl)-1-methyl-4(1H)-pyridone
1-methyl-3-(3-biphenylyl)-5-(3,3,3-trifluoro-1-propenyloxy)-4(1H)-pyridone
3-(3-iodophenoxy)-5-(3-biphenylyl)-1-methyl-4(1H)-pyridone
1-methyl-3-(2-methylphenoxy)-5-(3-biphenylyl)-4-(1H)-pyridinethione
1-methyl-3-(3-nitrophenyl)-5-(3-propylphenoxy)-4(1H)-pyridone
1-methyl-3-(3-hydroxyphenyl)-5-(3-propoxyphenoxy)-4(1H)-pyridone
3-benzyl-5-(3-methoxycarbonylphenyl)-1-methyl-4(1H)-pyridone
1-methyl-3-(3-phenylpropyl)-5-(3-propoxycarbonylphenyl)-4(1H)-pyridone
3-(3,5-diethylphenyl)-1-methyl-5-(4-trifluoromethoxyphenyl)-4(1H)-pyridinethione
3-(2,4-divinylphenyl)-5-[3-(2-fluoroethoxy)phenyl]-1-methyl-4(1H)-pyridinethione
3-[3-(3,3-dibromopropoxy)phenyl]-(3,5-dicyclopropylphenyl)-1-methyl-4(1H)-pyridone
3-(4-benzyloxyphenyl)-1-methyl-5-[3,5-di(isopropenyl)phenyl]-4(1H)-pyridinethione
3-(2,4-diformyloxyphenyl)-1-methyl-5-[3-(3-phenylpropoxy)phenyl]-4(1H)-pyridinethione
3-[3-(3-cyanopropoxy)phenyl]-5-(3-methoxy-5-iodophenyl)-1-methyl-4(1H)-pyridinethione
3-[3-(2-ethoxyethoxy)phenyl]-1-methyl-5-(3,4-diacetoxyphenyl)-4(1H)-pyridinethione
3-[2,4-di(2-propenyl)phenyl]-1-methyl-5-(3-vinyloxyphenyl)-4(1H)-pyridinethione
3-[3-(2-chloroallyloxy)phenyl]-1-methyl-5-(2,4-diethoxyphenyl)-4(1H)-pyridinethione 1-methyl-3-(3-ethoxycarbonylphenyl)-5-[4-(4,4,4-trifluoro-2-butenyloxy)phenyl]-4(1H)-pyridone
1-methyl-3-[3,5-di(chloromethyl)phenyl]-5-[2-(1,2,3-trichloro-3-butenyloxy)phenyl]-4(1H)-pyridinethione
3-[3-(4-chloro-2-butenyloxy)phenyl]-1-methyl-5-(3-fluoro-4-isobutoxyphenyl)-4(1H)-pyridone
3-[3-(3,3-dibromo-2-propenyloxy)phenyl]-1-methyl-5-(3-nitro-4-propylphenyl)-4(1H)-pyridinethione
3-(3-vinyloxyphenyl)-1-methyl-5-phenyl-4(1H)-pyridinethione, hydrobromide
3-[2,4-di(2-propenyl)phenyl]-5-(3-phenoxyphenyl)-1-methyl-4(1H)-pyridone
3-[3-(4-fluorophenoxy)phenyl]-1-methyl-5-phenyl-4(1H)-pyridinethione
1-methyl-3-(3-cyanomethyl-5-ethylphenyl)-5-[3-(3-iodophenoxy)phenyl]-4(1H)-pyridone
3-(3-methyl-5-fluorophenyl)-5-[3-(3-ethylphenoxy)phenyl]-1-methyl-4(1H)-pyridone
1-methyl-3-(2,4-difluorophenyl)-5-[2-(3-propoxyphenoxy)phenyl]-4(1H)-pyridinethione
1-methyl-3-[3-(2-nitrophenoxy)phenyl]-5-phenyl-4(1H)-pyridinethione
3-(3-isobutylthiophenyl)-1-methyl-5-phenyl-4(1H)-pyridinethione
3-(3-chloro-4-ethylthiophenyl)-5-[3-(4-cyanobutyl)phenyl]-1-methyl-4(1H)-pyridone
3-(2-chloro-4-ethylphenyl)-1-methyl-5-(3-methylthio-4-vinylphenyl)-4(1H)-pyridone
1-methyl-3-[3-(3-iodophenyl)phenyl]-5-(4-trifluoromethylthiophenyl)-4(1H)-pyridinethione
1-methyl-3-(3-cyclopentylphenyl)-5-[3-(2-fluoroethylthio)phenyl]-4(1H)-pyridinethione
3-(4-hydroxyphenyl)-1-methyl-5-[4-(3,3-dibromopropylthio)-3-nitrophenyl]-4(1H)-pyridone
3-[3,5-bis(4-phenylbutylthio)phenyl]-5-(2-methylphenyl)-1-methyl-4(1H)-pyridone
3-[2-bromo-4-(2-phenylethylthio)phenyl]-5-[3-(2-cyanopropylthio)-2-ethylphenyl]-1-methyl-4(1H)-pyridinethione
3-(3-acetoxy-5-ethylphenyl)-5-[2-(2-cyanopropylthio)phenyl]-1-methyl-4(1H)-pyridone
1-methyl-3-[3-(4-methoxybutylthio)phenyl]-5-phenyl-4(1H)-pyridinethione
1-methyl-3-[3-(3-phenylpropyl)phenyl]-5-[4-(2-isopropoxyethylthio)phenyl]-4(1H)-pyridone  3-(3-allylthio-4-methoxymethylphenyl)-5-[2-(2-cyanoethyl)-4-vinylphenyl]-1-methyl-4(1H)-pyridone
3-[3-(1,1-dichloroallylthio)phenyl]-5-[3-(2-butenyl)-2-propylphenyl]-1-methyl-4(1H)-pyridone
3-(4-ethyl-2-hydroxyphenyl)-5-[3-(2-chloro-3-butenylthio)-5-methoxyphenyl]-1-methyl-4(1H)-pyridone
1-methyl-3-(3-phenylthiophenyl)-5-phenyl-4(1H)-pyridinethione, hydrochloride
3-(3-chlorophenyl)-5-[3-(3-fluorophenylthio)phenyl]-1-methyl-4(1H)-pyridone
1-methyl-3-[3-(2-iodophenylthio)phenyl]-5-(3-methyl-5-methoxycarbonylphenyl)-4(1H)-pyridone
1-methyl-3-(2,4-diethylphenyl)-5-[3-(4-ethylphenylthio)-2-methoxyphenyl]-4(1H)-pyridone
3-[3-(3-isopropylphenylthio)phenyl]-5-phenyl-1-methyl-4(1H)-pyridone
1-methyl-3-(4-butylphenyl)-5-[3-(3-methoxyphenylthio)phenyl]-4(1H)-pyridinethione
3-(2-methyl-6-propoxyphenyl)-3-[3-(3-propoxyphenylthio)phenyl]-1-methyl-4(1H)-pyridone
3-[3-chloro-5-(4-nitrophenylthio)phenyl]-1-methyl-5-(2,4-divinylphenyl)-4(1H)-pyridone
3-(3-butylsulfinylphenyl)-5-phenyl-1-methyl-4(1H)-pyridone
1-methyl-3-(3-ethylsulfinylphenyl)-5-(4-propoxycarbonylphenyl)-4(1H)-pyridone
1-methyl-3-(2-nitrophenyl)-5-(3-trifluoromethylsulfinylphenyl)-4(1H)-pyridinethione
3-(2-ethoxyphenyl)-1-methyl-5-[3-(2-fluoroethylsulfinyl)-2-isopropylphenyl]-4(1H)-pyridone
3-phenyl-5-[3-(4,4-dibromobutylsulfinyl)-2-methoxyphenyl]-1-methyl-4(1H)-pyridone
3-(3-benzylsulfinylphenyl)-5-(3-chlorophenyl)-1-methyl-4(1H)-pyridone
3-(3,5-dimethylphenyl)-5-[3-(4-phenylbutylsulfinyl)phenyl]-1-methyl-4(1H)-pyridone
3-[3-(3-cyanopropylsulfinyl)phenyl]-1-methyl-5-phenyl-4(1H)-pyridinethione
3-(3-acetoxyphenyl)-5-[3-(2-cyanoethylsulfinyl)phenyl]-1-methyl-4(1H)-pyridone
3-(2-chloro-4-cyclohexylphenyl)-5-[3-chloro-5-(2-ethoxyethylsulfinyl)phenyl]-1-methyl-4(1H)-pyridinethione
1-methyl-3-[3-(4-methoxybutylsulfinyl)phenyl]-4(1H)-pyridone
3-(4-cyclopropylphenyl)-1-methyl-5-[3-(3-propoxypropylsulfinyl)phenyl]-4(1H)-pyridone
3-[3-(1,3-butadienylsulfinyl)phenyl]-1-methyl-5-phenyl-4(1H)-pyridinethione
1-methyl-3-[3-(2-butenylsulfinyl)phenyl]-5-(3-isobutylphenyl)-4(1H)-pyridone
1-methyl-3-[3-(2-bromoallylsulfinyl)phenyl]-5-(2,4-dimethylphenyl)-4(1H)-pyridinethione
1-methyl-3-(3-iodo-4-propylphenyl)-5-[3-(3,3,4,4-tetrafluoro-1-butenylsulfinyl)-5-ethylphenyl]-4(1H)-pyridone
1-methyl-3-(3-phenylsulfinylphenyl)-5-phenyl-4(1H)-pyridinethione
1-methyl-3-[3-(3-fluorophenylsulfinyl)phenyl]-5-[3-(2-propenyl)phenyl]-4(1H)-pyridone
3-[3-(3-isopropylphenylsulfinyl)phenyl]-5-phenyl-1-methyl-4(1H)-pyridone
3-[3-(2-ethoxyphenylsulfinyl)phenyl]-1-methyl-5-phenyl-4(1H)-pyridone
3-phenyl-1-methyl-5-[3-methoxy-5-(3-nitrophenylsulfinyl)phenyl]-4(1H)-pyridinethione
3-(3-cyclopropylmethylphenyl)-1-methyl-5-(2-trifluoromethylphenyl)-4(1H)-pyridone
3,5-bis[3-(2-cyclopentylethyl)phenyl]-1-methyl-4(1H)-pyridone
3-(3-cyclopropoxyphenyl)-1-methyl-5-(2-fluorophenyl)-4(1H)-pyridinethione
3-(3-cyclohexyloxyphenyl)-1-methyl-5-phenyl-4(1H)-pyridone, methanesulfonate
3-(4-chlorophenyl)-5-(3-cyclobutylthiophenyl)-1-methyl-4(1H)-pyridone
3-(3-cyclopentylsulfinylphenyl)-5-(3-butylphenyl)-1-methyl-4(1H)-pyridone, hydrochloride
1-methyl-3-(3-cyclopropylmethoxyphenyl)-5-(3-trifluoromethylphenyl)-4(1H)-pyridone
1-methyl-3-[3-(2-cyclohexylethoxy)phenyl]-5-phenyl-4(1H)-pyridone, hydrobromide
3-[3-(2-cyclobutylethylthio)phenyl]-1-methyl-5-(3,5-dimethylphenyl)-4(1H)-pyridone
3-(3-cyclopentylmethylsulfinylphenyl)-1-methyl-5-(3-trifluoromethylphenyl)-4(1H)-pyridone
3-cyclopropylmethyl-5-(3-fluorophenyl)-1-methyl-4(1H)-pyridone, methanesulfonate
3-(3-chlorophenyl)-5-(2-cyclohexylethyl)-1-methyl-4(1H)-pyridone 3-(3-fluorophenyl)-1-methyl-5-phenylthio-4(1H)-pyridone
3-(3-chloro-5-methylphenyl)-1-methyl-5-phenylsulfinyl-4(1H)-pyridone
3-(3-butylphenyl)-5-(3,5-dichlorophenylthio)-1-methyl-4(1H)-pyridone
3-(3,4-dibromophenyl)-1-methyl-5-(4-ethylphenylsulfinyl)-4(1H)-pyridinethione
1-methyl-3-(3-fluorophenyl)-5-(3-propoxyphenylsulfinyl)-4(1H)-pyridinethione
3-(3-chlorophenyl)-1-methyl-5-propylsulfinyl-4(1H)-pyridinethione, hydrofluoride
1-methyl-3-(3-fluorophenyl)-5-trifluoromethylthio-4(1H)-pyridinethione, toluenesulfonate
3-(2-chloroethylsulfinyl)-1-methyl-5-(3-methylphenyl)-4(1H)-pyridone
3-(2-bromopropylsulfinyl)-1-methyl-5-(3-ethylphenyl)-4(1H)-pyridinethione
1-methyl-3-(2,3-dimethylphenyl)-5-vinylthio-4(1H)-pyridone
3-allylsulfinyl-3-(3,5-diiodophenyl)-1-methyl-4(1H)-pyridinethione
1-methyl-3-(3-trifluoromethylphenyl)-5-vinylsulfinyl-4(1H)-pyridinethione
3-(3-allylphenyl)-5-(2-chlorovinylthio)-1-methyl-4(1H)-pyridinethione
1-methyl-3-(2-chloro-3-fluorophenyl)-5-(1,2-difluoroallylsulfinyl)-4(1H)-pyridone
3-(2-bromo-1-propenylsulfinyl)-1-methyl-5-(3-methylphenyl)-4(1H)-pyridinethione
1-methyl-3-(2-propoxyvinyl)-5-(3-trifluoromethylphenyl)-4(1H)-pyridone.
3-(6-ethoxy-2-hexenyl)-1-methyl-5-(3-chlorophenyl)-4(1H)-pyridinethione, hydrochloride The following are the preferred compounds of the invention.

1-methyl-3-phenyl-5-(3-trifluoromethylphenyl)-4(1H)-pyridone
3-(3-fluorophenyl)-1-methyl-5-phenyl-4(1H)-pyridone
3-(3-chlorophenyl)-1-methyl-5-phenyl-4(1H)-pyridone
3,5-bis(3-chlorophenyl)-1-methyl-4(1H)-pyridone
3-(3-chlorophenyl)-5-(3-fluorophenyl)-1-methyl-4(1H)-pyridone
1-methyl-3-(3-methylphenyl)-5-phenyl-4(1H)-pyridone
1-methyl-3,5-bis(3-trifluoromethylphenyl)-4(1H)-pyridone
3-(3-bromophenyl)-1-methyl-5-phenyl-4(1H)-pyridone
3-(3-methoxyphenyl)-1-methyl-5-phenyl-4(1H)-pyridone
3-(3-ethoxyphenyl)-1-methyl-5-phenyl-4(1H)-pyridone
1-methyl-3-phenyl-5-(3-propoxyphenyl)-4(1H)-pyridone
3-(3-isopropoxyphenyl)-1-methyl-5-phenyl-4(1H)-pyridone
1-methyl-3-phenyl-5-[3-(1,1,2,2-tetrafluoroethoxy)phenyl]-4(1H)-pyridone
3,5-bis(3-fluorophenyl)-1-methyl-4(1H)-pyridone
3-(2-chlorophenyl)-1-methyl-5-(3-trifluoromethylphenyl)-4(1H)-pyridone
3-(3-chlorophenyl)-1-methyl-5-(3-trifluoromethylphenyl)-4(1H)-pyridone
3-(4-chlorophenyl)-1-methyl-5-(3-trifluoromethylphenyl)-4(1H)-pyridone
3-(2-fluorophenyl)-1-methyl-5-(3-trifluoromethylphenyl)-4(1H)-pyridone
3-(3-fluorophenyl)-1-methyl-5-(3-trifluoromethylphenyl)-4(1H)-pyridone
3-(4-fluorophenyl)-1-methyl-5-(3-trifluoromethylphenyl)-4(1H)-pyridone
3-(3-chlorophenyl)-5-(4-chlorophenyl)-1-methyl-4(1H)-pyridone
1-methyl-3-(3-trifluoromethylphenyl)-4(1H)-pyridone
1,3-dimethyl-5-(3-trifluoromethylphenyl)-4(1H)-pyridone
3-ethyl-1-methyl-5-(3-trifluoromethylphenyl)-4(1H)-pyridone
1-methyl-3-(3-methylthiophenyl)-5-phenyl-4(1H)-pyridone
3-(4-chloro-3-trifluoromethylphenyl)-1-methyl-5-phenyl-4(1H)-pyridone
3-(2-chlorophenyl)-5-(3-chlorophenyl)-1-methyl-4(1H)-pyridone
3-(3-bromophenyl)-5-(3-chlorophenyl)-1-methyl-4(1H)-pyridone
3-(3-bromophenyl)-1-methyl-5-(2-methylphenyl)-4(1H)-pyridone
3-(3-chlorophenyl)-1-methyl-5-(2-methylphenyl)-4(1H)-pyridone
1-methyl-3,5-bis(3-methylphenyl)-4(1H)-pyridone
3-(2-bromophenyl)-1-methyl-5-(3-trifluoromethylphenyl)-4(1H)-pyridone
1-methyl-3-(2-methylphenyl)-5-(3-trifluoromethylphenyl)-4(1H)-pyridone
3-(2-ethylphenyl)-1-methyl-5-(3-trifluoromethylphenyl)-4(1H)-pyridone
1-methyl-3-(2-trifluoromethylphenyl)-5-(3-trifluoromethylphenyl)-4(1H)-pyridone
3-(2-methoxyphenyl)-1-methyl-5-(3-trifluoromethylphenyl)-4(1H)-pyridone
3-(3-bromophenyl)-1-methyl-5-(3-trifluoromethylphenyl)-4(1H)-pyridone
1-methyl-3-(3-methylphenyl)-5-(3-trifluoromethylphenyl)-4(1H)-pyridone
1-methyl-3-(4-methylphenyl)-5-(3-trifluoromethylphenyl)-4(1H)-pyridone
3-(3-isobutylphenyl)-1-methyl-5-phenyl-4(1H)-pyridone
1-methyl-3-propyl-5-(3-trifluoromethylphenyl)-4(1H)-pyridone
3-methoxy-1-methyl-5-(3-trifluoromethylphenyl)-4(1H)-pyridone
3-ethoxy-1-methyl-5-(3-trifluoromethylphenyl)-4(1H)-pyridone
3-isopropoxy-1-methyl-5-(3-trifluoromethylphenyl)-4(1H)-pyridone
1-methyl-3-phenoxy-5-(3-trifluoromethylphenyl)-4(1H)-pyridone
3-(4-chloro-3-trifluoromethylphenyl)-5-ethoxy-1-methyl-4(1H)-pyridone
1-methyl-3-(4-chloro-3-trifluoromethylphenyl)-5-propyl-4(1H)-pyridone
3-ethyl-1-methyl-5-(4-chloro-3-trifluoromethylphenyl)-4(1H)-pyridone
3-ethylthio-1-methyl-5-(3-trifluoromethylphenyl)-4(1H)-pyridone
1-methyl-3-propylthio-5-(3-trifluoromethylphenyl)-4(1H)-pyridone
1-methyl-3-allylthio-5-(3-trifluoromethylphenyl)-4(1H)-pyridone
1-methyl-3-isopropylthio-5-(3-trifluoromethylphenyl)-4(1H)-pyridone
3-ethylsulfinyl-1-methyl-5-(3-trifluoromethylphenyl)-4(1H)-pyridone
1-methyl-3-(3-trifluoromethylphenyl)-5-trifluoromethylthio-4(1H)-pyridone 1-methyl-3-(2-chloro-4-fluorophenyl)-5-(3-trifluoromethylphenyl)-4(1H)-pyridone
3-(2,5-dimethylphenyl)-1-methyl-5-(3-trifluoromethylphenyl)-4(1H)-pyridone
3-(3,4-dimethylphenyl)-1-methyl-5-(3-trifluoromethylphenyl)-4(1H)-pyridone
1-methyl-3-(3-methylthiophenyl)-5-(3-trifluoromethylphenyl)-4(1H)-pyridone
3-isopropyl-1-methyl-5-(3-trifluoromethylphenyl)-4(1H)-pyridone
1-methyl-3-phenyl-5-(3-trifluoromethylphenyl)-4(1H)-pyridinethione
3-(3,5-dichlorophenoxy)-1-methyl-5-(3-trifluoromethylphenyl)-4(1H)-pyridone
1-methyl-3-(2,2,2-trifluoroethoxy)-5-(3-trifluoromethylphenyl)-4(1H)-pyridone The compounds of this invention can be prepared by various synthetic routes. Benary and Bitter, *Ber.* 61, 1058 (1928) taught the synthesis of an intermediate disodium salt of 1,5-dihydroxy-2,4-diphenyl-1,4-pentadien-3-one by the condensation of 1,3-diphenyl-2-propanone with ethyl formate in the presence of sodium methoxide. The intermediate pentadienone is neutralized by strong acid and forms 3,5-diphenyl-4-pyrone. Reaction of the pyrone with ammonium acetate at an elevated temperature produces 3,5-diphenyl-4(1H)-pyridone.

Alternatively, 3,5-diphenyl-4(1H)-pyridones can be prepared by the reaction of an appropriately ring-substituted 1,3-diphenyl-2-propanone with formamide and formamidine acetate. Reaction at reflux temperature produces the corresponding 3,5-diphenyl-4(1H)-pyridone, which is reacted with a methyl halide in the presence of a suitable strong base to form the desired compound.

A preferred synthesis of the compounds is adapted from the methods of Benary and Bitter and of El-Kholy et al., cited above. An appropriately substituted 1-phenyl-2-propanone is formylated at low temperature with sodium methoxide and ethyl formate in ether, and the product is treated with a salt of methylamine in aqueous medium. The resulting intermediate is predominantly a 1-methyl-2-phenyl-1-buten-3-one. Some pyridone is also formed at this step, as reported by El-Kholy et al. The butenone is reformylated as before, and spontaneously cyclizes to form the 1-methyl-3-phenyl-4(1H)-pyridone.

Another preferred synthesis is similar to the above, but uses an aminoformylation step instead of formylation. A preferred aminoformylation agent is a formiminium halide, such as the reaction product of phosgene and dimethylformamide. The propanone is diaminoformylated, and the intermediate is exchanged with methylamine or a salt thereof and hydrolyzed with acid or alkali to form the 1-methyl-3-phenyl-4(1H)-pyridone.

The starting 2-propanones may be prepared by syntheses in the literature. For example, see Coan et al., *J. Am. Chem. Soc.* 76, 501 (1954); Sullivan et al., "Disodium Tetracarbonylferrate", *American Laboratory* 49–56 (June 1974); Collman et al., "Synthesis of Hemifluorinated Ketones using Disodium Tetracarbonylferrate," *J. Am. Chem. Soc.* 95, 2689–91 (1973); Collman et al., "Acyl and Alkyl Tetracarbonylferrate Complexes as Intermediates in the Synthesis of Aldehydes and Ketones", *J. Am. Chem. Soc.* 94, 2516–18 (1972).

The general synthesis methods of the compounds proceed from either ketone starting compounds or from carbonyl halides. The general process is the same, whichever starting compound is used. The general process, of which the preferred synthesis described above is an embodiment, will be discussed first. Reagents and reaction conditions will then be explained in detail, and some preparative examples will be illustrated.

The synthesis proceeds through an intermediate of the formula

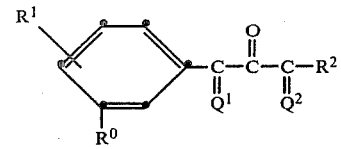

wherein
$Q^1$ and $Q^2$ independently represent 2 hydrogen atoms,
=CHOH, or an alkali metal salt thereof,
=CHN($R^9$)$_2$ or
=CHNHCH$_3$, provided that only one of $Q^1$ and $Q^2$ represents =CHNHCH$_3$.

The $R^9$ groups independently represent $C_1$–$C_3$ alkyl, or the $R^9$ groups combine with the nitrogen atom to which they are attached to form pyrrolidino, piperidino, morpholino, N-methylpiperazino and the like.

The =CHOH groups, which may be in the form of alkali metal salts, are provided by reaction with formylating agents which will be defined below. The =CHN($R^9$)$_2$ groups are provided by reaction with amino-formylating agents, and the =CHNHCH$_3$ groups are provided by exchanging either =CHOH groups or =CHN($R^9$)$_2$ groups with methylamine.

The intermediates described above are prepared from either ketones or carbonyl halides, as will be explained below. When $Q^1$ and $Q^2$ each represent 2 hydrogen atoms, the pyridones are prepared by either 1. reacting with a formylating or amino-formylating agent;
2. reacting again with a formylating or amino-formylating agent; and
3. reacting with methylamine; or 1. reacting with a formylating or amino-formylating agent;
2. reacting with methylamine; and
3. reacting again with a formylating or amino-formylating agent.

When one of $Q^1$ and $Q^2$ represents either =CHOH or =CHN($R^9$)$_2$, and the other represents 2 hydrogen atoms, the pyridones are prepared by either 1. reacting with a formylating or amino-formylating agent; and
2. reacting with methylamine; or
1. reacting with methylamine; and
2. reacting with a formylating or amino-formylating agent.

When each of $Q^1$ and $Q^2$ represent either =CHOH or =CHN($R^9$)$_2$, the pyridones are prepared by reacting with methylamine.

The variations of the synthesis, and the preparation of the intermediates, will be sketched below.

When the process starts with a ketone of the general formula

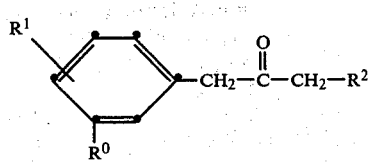

the first step is the formylation or aminoformylation of one of the methylene groups. If a formylating agent is used, a ketone of the formula

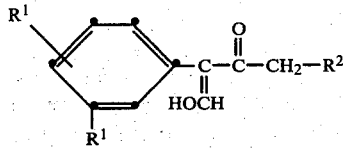

is produced. Reaction with an aminoformylating agent produces an enaminoketone such as (III) below.

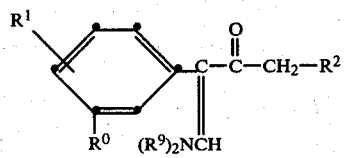

Organic chemists will understand that, although the sketches above show the first formylation or aminoformylation as occurring on a certain side of the ketone, it may in fact occur on either side of the ketone, depending on the activating characteristics of $R^0$, $R^1$ and $R^2$. The course of the reaction is the same in either case. It will also be understood that, in many instances, the product of the formylation or aminoformylation step will actually be a mixture containing the two possible monosubstituted compounds and the disubstituted compound.

The monosubstituted product is formylated or aminoformylated again, and exchanged with methylamine. The steps may be performed in either order. If the exchange is performed first, the intermediate product is an enaminoketone of the formula

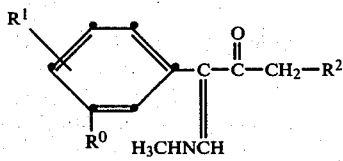

Either formylation or aminoformylation of the above enaminoketone affords the pyridone product, as the intermediate cyclizes as soon as the second group is introduced on the other methylene group.

Alternatively, either of compounds (II) or (III) may be either formylated or aminoformylated to provide intermediates of any of the formulae below.

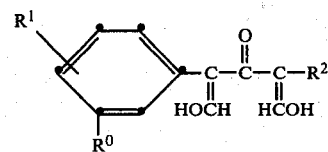

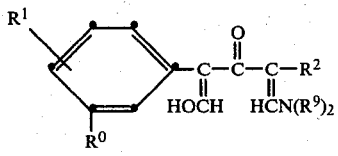

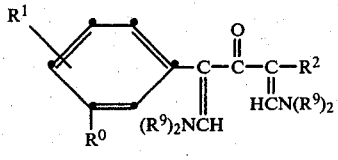

It will be understood that the compound similar to (VI), wherein the formyl and aminoformyl groups are reversed, is equivalent in all respects to compound (VI). Pyridones are formed from any of the above three intermediates by simple contact of the intermediate with methylamine.

When the starting compound is a carbonyl halide, the process proceeds essentially as described above, except for a first step performed as follows:

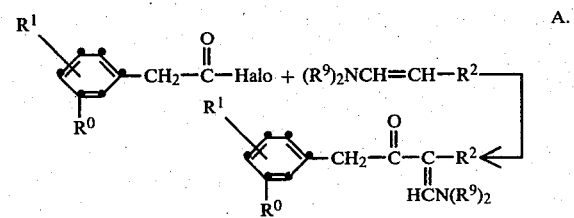

It will be understood that reaction (A) can also be performed in the opposite manner, as shown below:

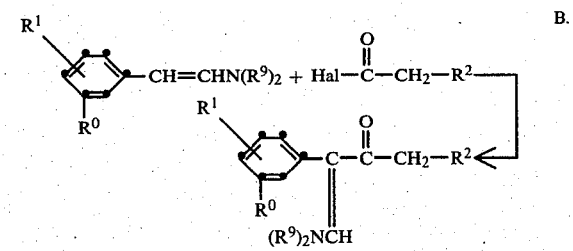

It is also possible to form intermediates using phosgene as the carbonyl halide when the 3- and 5-substituents of the pyridone product are identical.

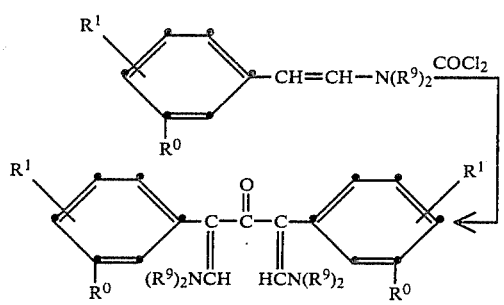

The enaminoketones formed in equations (A), (B) and (C) above are identical to the intermediates described in (III) and (VII) above, and are converted to the pyridone products as described above.

Alternatively, it is possible to prepare the 1-unsubstituted pyridones by using $NH_3$ in place of methylamine in the process, or by using the process of Benary and Bitter. The pyridone is then alkylated at the 1-position with a methyl halide, or with a dimethyl sulfate, according to common procedures.

An alternative method of alkylation proceeds by converting the 1-unsubstituted pyridone to the 4-halo or 4-alkoxy derivative by reaction with a halogenating agent, or an O-alkylating agent. Suitable halogenating agents include such agents as $POCl_3$, $POBr_3$, $PCl_5$ and the like. O-alkylating agents include such reagents as methyl trifluoromethanesulfonate, methyl fluorosulfonate and the like, as well as alkyl halides used in the presence of base. In the next step, the 4-halo or 4-alkoxy compound is reacted with a methyl halide to form the 1-methyl-substituted, 4-substituted pyridinium salt. The salt is then hydrolyzed with either a mineral acid or an alkali metal hydroxide to produce the desired product. See, for example, Takahashi et al., Pharm. Bull. (Japan) 1, 70–74 (1953).

As a chemist would expect, methylamine may be used in the form of salts, preferably hydrohalide salts, including hydrochlorides, hydrobromides and the like. Such salts are often more convenient than the free amines.

The formylating agents used in the process are chosen from the common agents used for such reactions. The preferred formylating agents are esters of formic acid of the formulae

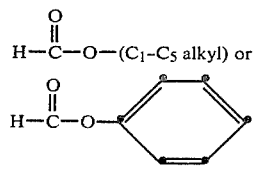

Similar formylations are discussed in Organic Syntheses 300-02 (Collective Vol. III 1955).

The esters are used in the presence of strong bases, of which alkali metal alkoxides are preferred, such as sodium methoxide, potassium ethoxide and lithium propoxide. Other bases may also be used, including alkali metal hydrides, alkali metal amides, and inorganic bases including alkali metal carbonates and hydroxides. Such strong organic bases as diazabicyclononane and diazabicycloundecane are also useful.

Reactions with formylating agents are performed in aprotic solvents such as are regularly used in chemical synthesis. Ethyl ether is usually the preferred solvent. Ethers in general, including solvents such as ethyl propyl ether, ethyl butyl ether, 1,2-dimethoxyethane and tetrahydrofuran, aromatic solvents such as benzene and xylene, and alkanes such as hexane and octane can be used as formylation solvents.

Because of the strong bases used in the formylation reactions, low temperatures produce the best yields. Reaction at temperatures in the range of from about −25° C. to about 10° C. is preferred. The reaction mixture may be allowed to warm to room temperature, however, after the reaction has proceeded part way to completion. Reaction times from about 1 to about 24 hours are adequate for economic yields in the formylation reactions.

The aminoformylating agents used in these syntheses may be any compounds capable of reacting with an active methylene group to introduce a $=CHN(R^9)_2$ group, or its acid addition salt. Such agents are chosen from among s-triazine, the orthoformamides,

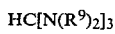

the formate ester aminals,

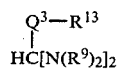

the formamide acetals,

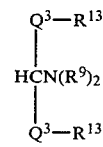

the tris(formylamino)methanes,

and preferably from the formiminium halides,

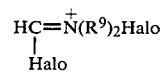

$Q^3$ in the structures above represents oxygen or sulfur, and $R^{13}$ represents $C_1$–$C_6$ alkyl or phenyl.

Useful references on the aminoformylating agents include DeWolfe, Carboxylic Acid Derivatives 420-506 (Academic Press 1970), and Ulrich, Chemistry of Imidoyl Halides 87-96 (Plenum Press 1968). Bredereck et al. have written many papers on such agents and reactions, of which the following are typical. Ber. 101, 4048-56 (1968); Ber. 104, 2709-26 (1971); Ber. 106, 3732-42 (1973); Ber. 97, 3397-406 (1964); Ann. 762, 62-72 (1972); Ber. 97, 3407-17 (1964); Ber. 103, 210-21 (1970); Angew. Chem. 78, 147 (1966); Ber. 98, 2887-96 (1965); Ber. 96, 1505-14 (1963); Ber. 104, 3475-85 (1971); Ber. 101, 41-50 (1968); Ber. 106, 3725-31 (1973); and Angew. Chem. Int'l. Ed. 5, 132 (1966). Other notable papers on the subject include Kreutzberger et al., Arch. der Pharm. 301, 881-96 (1968), and 302, 362-75 (1969), and Weingarten et al., J. Org. Chem. 32, 3293-94 (1967).

Aminoformylations are usually carried out without solvent, at elevated temperatures from about 50° C. to about 200° C. Solvents such as dimethylformamide are sometimes used, however, particularly when it is desirable to raise the boiling point of the reaction mixture.

When aminoformylating with formiminium halides, however, aprotic solvents, such as described above in the description of solvents for formylation, are used at temperatures from about 0° C. to about 80° C., preferably above room temperature. Halogenated solvents such as chloroform and methylene chloride can also be used in such aminoformylations if desired.

The exchange reactions with methylamine are best performed in protic solvents of which alkanols are preferred and ethanol is most appropriate. Temperatures from about −20° C. to about 100° C. can be used for the exchange reactions. Room temperature is satisfactory.

In general, intermediate compounds in the synthesis are not purified, but are simply used in successive steps after separation by extraction, neutralization or removal of excess solvent or reactant as appropriate.

The enamine acylation reactions, A–C, are performed in the presence of bases such as tertiary amines, alkali metal carbonates, magnesium oxide and the like, and in aprotic solvents as described above.

In some instances, as organic chemists will understand, it is necessary to apply additional synthetic steps after the pyridone compound has been formed. For example, it is convenient to form compounds having alkoxy, alkanoyloxy and like $R^0$, $R^1$ and $R^5$ substituents by first making the corresponding hydroxy-substituted compound, and then substituting on the oxygen atom.

The pyridinethiones are readily prepared by the treatment of the corresponding pyridones with $P_2S_5$ in pyridine at reflux temperature, according to known methods.

The following preparative examples are presented to assure that those skilled in organic chemistry can obtain any desired compound of this invention.

The examples below show the various processes by which compounds of the invention have been made. It will be understood, however, that all of the various processes can be used, with appropriate variations, to make any compound of the invention.

Many exemplary compounds are indicated as made by the general process of a previous exemplary compound. In such instances, an ordinarily skilled organic chemist will readily see the minor changes to the exemplary process which will be needed to prepare the other exemplary compounds.

The first example below illustrates the preparation of a compound by a preferred synthetic process.

EXAMPLE 1

1-methyl-3-phenyl-5-(3-trifluoromethylphenyl)-4(1H)-pyridone

A 30 ml. portion of phosgene was combined with 135 ml. of chloroform and cooled to −10° C. The temperature was held approximately constant while 23 ml. of dimethylformamide was added dropwise. After the addition, a solution of 32 g. of 1-phenyl-3-(3-trifluoromethylphenyl)-2-propanone in 40 ml. of chloroform was added, and the reaction mixture was stirred under reflux at 62° C. for 90 minutes. The reaction mixture was then cooled, and to it was added 40 ml. of water, 17 ml. of 25 percent aqueous sodium hydroxide, and 26 ml. of 40 percent aqueous methylamine. The mixture was stirred and heated to 100° C. to distill off the solvent.

The reaction mixture was then cooled, and to it was added 135 ml. of denatured ethanol, 26 ml. of 40 percent aqueous methylamine, and 24 g. of sodium hydroxide. The mixture was then stirred under reflux at 78° C. for 3 hours, and was then cooled. One hundred ml. of additional water was added, and the reaction mixture was heated at 100° C. to distill off the ethanol.

The mixture was then cooled again, and to it was added 200 ml. of dichloromethane. The layers were separated, and the organic layer was washed with 25 ml. of 5 percent aqueous hydrochloric acid. The layers were separated again, and the organic layer was evaporated to an oily residue under vacuum at 55° C. The residue was cooled, and triturated with 100 ml. of water, and 200 ml. of diethyl ether. The product precipitated, and was recovered by filtration. The crude product was washed on the filter with 100 ml. of water and 200 ml. of diethyl ether and vacuum dried at 50° C. to produce 30.3 g. of 1-methyl-3-phenyl-5-(3-trifluoromethylphenyl)-4(1H)-pyridone, m.p. 149°–151° C.

The following example illustrates another preferred method of synthesis.

EXAMPLE 2

1-methyl-3-phenyl-5-(3-trifluoromethylphenyl)-4(1H)-pyridone

A 27.8 g. portion of 1-phenyl-3-(3-trifluoromethylphenyl)-2-propanone was dissolved in 100 ml. of dichloromethane, and was added to a solution of 10.8 g. of sodium methoxide in 100 ml. of dichloromethane under nitrogen. The mixture was stirred for one hour at room temperature, and was then cooled to 5° C. A 12 g. portion of methyl formate was added, while the temperature was held between 0° C. and 5° C. The mixture was then stirred overnight while the temperature was allowed to rise to the ambient temperature. A 13.4 g. portion of methylamine hydrochloride in 50 ml. of water was added, and the mixture was stirred for 30 minutes. The layers were then separated, and the organic layer was subjected to the methoxide, formate and methylamine treatments two additional times. After the second repetition of the process, the organic phase was evaporated to dryness under vacuum, and the residue was crystallized from diethyl ether to obtain 18 g. of 1-methyl-3-phenyl-5-(3-trifluoromethylphenyl)-4(1H)-pyridone, m.p. 152°–153° C.

The process of Example 2 was also used to produce the compounds below.

EXAMPLE 3

1-methyl-3,5-bis(3-trifluoromethylphenyl)-4(1H)-pyridone, m.p. 152°–154° C., yield 39%.

EXAMPLE 4

3-(3-bromophenyl)-5-(3-chlorophenyl)-1-methyl-4(1H)-pyridone, m.p. 192° C., yield 23%.

EXAMPLE 5

3-(3-chlorophenyl)-5-(4-chlorophenyl)-1-methyl-4(1H)-pyridone, m.p. 170°–172° C., yield 26%.

EXAMPLE 6

3-(2-fluorophenyl)-1-methyl-5-(3-trifluoromethylphenyl)-4(1H)-pyridone, m.p. 152°–154° C., yield 20%.

EXAMPLE 7

3-(2-chlorophenyl)-5-(3-chlorophenyl)-1-methyl-4(1H)-pyridone, m.p. 160°–161° C., yield 15%.

EXAMPLE 8

3-(3-methoxyphenyl)-1-methyl-5-(3-trifluoromethylphenyl)-4(1H)-pyridone, m.p. 113°–115° C., yield 7%.

EXAMPLE 9

3-(4-chlorophenyl)-1-methyl-5-(3-trifluoromethylphenyl)-4(1H)-pyridone, m.p. 153°–155° C., yield 26%.

EXAMPLE 10

3-(2-chlorophenyl)-1-methyl-5-(3-trifluoromethylphenyl)-4(1H)-pyridone, m.p. 191°–193° C., yield 14%.

EXAMPLE 11

3-(3-fluorophenyl)-1-methyl-5-(3-trifluoromethylphenyl)-4(1H)-pyridone, m.p. 94°–96° C., yield 13%.

EXAMPLE 12

3-(4-fluorophenyl)-1-methyl-5-(3-trifluoromethylphenyl)-4(1H)-pyridone, m.p. 113°–134° C., yield 29%.

EXAMPLE 13

3-(4-methoxyphenyl)-1-methyl-5-(3-trifluoromethylphenyl)-4(1H)-pyridone, m.p. 162°–165° C., yield 33%.

EXAMPLE 14

3-(3-fluorophenyl)-1-methyl-5-phenyl-4(1H)-pyridone, m.p. 133.5° C., yield 69%.

EXAMPLE 15

3-(3-chlorophenyl)-1-methyl-5-phenyl-4(1H)-pyridone, m.p. 172.5° C., yield 27%.

EXAMPLE 16

3,5-bis(3-chlorophenyl)-1-methyl-4(1H)-pyridone, m.p. 164°–167° C., yield 59%.

EXAMPLE 17

1-methyl-3-(3-methylphenyl)-5-phenyl-4(1H)-pyridone (complex containing ½ mole of benzene), m.p. 79.5° C., yield 25%.

EXAMPLE 18

3-(3-methoxyphenyl)-1-methyl-5-phenyl-4(1H)-pyridone, NMR peaks at 200 and 220 CPS; aromatic protons at 420–440 and 442–460 CPS; yield 33%.

EXAMPLE 19

3-(3,4-dichlorophenyl)-1-methyl-5-phenyl-4(1H)-pyridone, m.p. 166.5° C., yield 54%.

EXAMPLE 20

3-(2,5-dichlorophenyl)-1-methyl-5-phenyl-4(1H)-pyridone, m.p. 155.5° C., yield 22%.

EXAMPLE 21

3,5-bis(3-fluorophenyl)-1-methyl-4(1H)-pyridone, m.p. 149°–151° C., yield 60%.

EXAMPLE 22

3-(3-chlorophenyl)-5-(3-fluorophenyl)-1-methyl-4(1H)-pyridone, m.p. 145°–146° C., yield 64%.

EXAMPLE 23

3-(3,5-dichlorophenyl)-1-methyl-5-phenyl-4(1H)-pyridone, m.p. 131°–135° C., yield 28%.

EXAMPLE 24

3,5-bis(3-bromophenyl)-1-methyl-4(1H)-pyridone, m.p. 216.5° C., yield 43%.

EXAMPLE 25

3-(3-bromophenyl)-1-methyl-5-phenyl-4(1H)-pyridone, m.p. 172° C., yield 38%.

EXAMPLE 26

3-(3-bromophenyl)-1-methyl-5-(3-trifluoromethylphenyl)-4(1H)-pyridone, m.p. 151°–153° C., yield 37%.

EXAMPLE 27

3-(3-chlorophenyl)-1-methyl-5-(3-trifluoromethylphenyl)-4(1H)-pyridone, m.p. 133°–135° C., yield 28%.

EXAMPLE 28

3-(3-biphenylyl)-1-methyl-5-phenyl-4(1H)-pyridone, m.p. 186°–190° C., yield 2%.

The following example illustrates the synthesis of pyridones by the di(aminoformylation) of ketones, followed by exchange with amines.

EXAMPLE 29

1-methyl-3-(2-methylphenyl)-5-(3-trifluoromethylphenyl)-4(1H)-pyridone

A mixture of 8 g. of 1-(2-methylphenyl)-3-(3-trifluoromethylphenyl)-2-propanone and 25 ml. of dimethylformamide dimethyl acetal was heated under reflux for 12 hours. Analysis of the reaction mixture showed that the reaction had gone in large part to the desired 1,5-di(dimethylamino)-2-(2-methylphenyl)-4-(3-trifluoromethylphenyl)-1,4-pentadiene-3-one. The intermediate was used without purification; 10 g. of methylamine hydrochloride was added to the original reaction mixture, methanol was added, and the mixture was heated under reflux for 14 hours. The reaction mixture was then purified by chromatography over a silica gel column, eluting with 1:1 ethyl acetate: benzene. The product-containing fractions were combined, and were evaporated to dryness to obtain 0.8 g. of 1-methyl-3-(2-methylphenyl)-5-(3-trifluoromethylphenyl)-4(1H)-pyridone, m.p. 144°–147° C.

The procedure of Example 29 was used to prepare the following compounds.

EXAMPLE 30

1-methyl-3-(3-trifluoromethylphenyl)-4(1H)-pyridone, m.p. 122°–123° C., yield 16%.

EXAMPLE 31

3-(3-ethoxycarbonylphenyl)-1-methyl-5-phenyl-4(1H)-pyridone, m.p. 167°–168° C., yield 11%.

EXAMPLE 32

1-methyl-3-(3-methylphenyl)-5-(3-trifluoromethylphenyl)-4(1H)-pyridone, m.p. 155°–157° C., yield 2.4%.

EXAMPLE 33

1-methyl-3-(4-methylphenyl)-5-(3-trifluoromethylphenyl)-4(1H)-pyridone, m.p. 154°–156° C., yield 6%.

EXAMPLE 34

5-(3-methoxycarbonylphenyl)-1-methyl-3-(4-methylphenyl)-4(1H)-pyridone, m.p. 85°–88° C., yield 5%.

EXAMPLE 35

5-(3-methoxycarbonylphenyl)-1-methyl-3-(3-methylphenyl)-4(1H)-pyridone, m.p. 180°–183° C., yield 1%.

EXAMPLE 36

3-methoxy-1-methyl-5-(3-trifluoromethylphenyl)-4(1H)-pyridone, m.p. 173°–175° C., yield 18%.

EXAMPLE 37

3-(4-bromophenyl)-1-methyl-5-(3-methylphenyl)-4(1H)-pyridone, m.p. 201°–204° C., yield 21%.

EXAMPLE 38

3-(3,4-dichlorophenyl)-1-methyl-5-(3-trifluoromethylphenyl)-4(1H)-pyridone, m.p. 109°–112° C., yield 4%.

EXAMPLE 39

3,5-bis(3,5-dichlorophenyl)-1-methyl-4(1H)-pyridone, m.p. 275°–278° C., yield 14%.

EXAMPLE 40

3-(3,4-dichlorophenyl)-1-methyl-5-(3-methylphenyl)-4(1H)-pyridone, mass spectrometry MI, 342, yield 10%.

EXAMPLE 41

3-(3,4-dichlorophenyl)-5-(3,4-dimethylphenyl)-1-methyl-4(1H)-pyridone, m.p. 150°–152° C., yield 6%.

EXAMPLE 42

3-(3-chlorophenyl)-1-methyl-5-(2-methylphenyl)-4(1H)-pyridone, m.p. 171°–173° C., yield 12%.

EXAMPLE 43

3-(4-bromophenyl)-1-methyl-5-(3-trifluoromethylphenyl)-4(1H)-pyridone, m.p. 144°–146° C., yield 30%.

EXAMPLE 44

3-(3-chlorophenyl)-1-methyl-5-(4-trifluoromethylphenyl)-4(1H)-pyridone, m.p. 147°–151° C., yield 2%.

EXAMPLE 45

3-(3-methylphenyl)-5-(4-methylphenyl)-1-methyl-4(1H)-pyridone, m.p. 155°–157° C., yield 28%.

EXAMPLE 46

1-methyl-3-(3-chlorophenyl)-5-(3,4-dichlorophenyl)-4(1H)-pyridone, m.p. 107°–110° C., yield 10%.

EXAMPLE 47

1-methyl-3-(3,4-dichlorophenyl)-5-(2-methylphenyl)-4(1H)-pyridone, m.p. 103°–106° C., yield 10%.

EXAMPLE 48

1-methyl-3-(2-chlorophenyl)-5-(3,4-dichlorophenyl)-4(1H)-pyridone, m.p. 169°–171° C., yield 25%.

EXAMPLE 49

1-methyl-3-(3-bromophenyl)-5-(3,4-dichlorophenyl)-4(1H)-pyridone, m.p. 152°–154° C., yield 10%.

EXAMPLE 50

1-methyl-3-(3,5-dichlorophenyl)-5-(3-trifluoromethylphenyl)-4(1H)-pyridone, m.p. 156°–160° C., yield 30%.

EXAMPLE 51

1-methyl-3-(3-bromophenyl)-5-(3-methylphenyl)-4(1H)-pyridone, m.p. 144°–147° C., yield 3%.

EXAMPLE 52

1-methyl-3,5-bis(3-methylphenyl)-4(1H)-pyridone, m.p. 148°–150° C., yield 8%.

EXAMPLE 53

1-methyl-3-(3-fluorophenyl)-5-(2,5-dimethylphenyl)-4(1H)-pyridone, mass spectroscopy MI, 307, yield 10%.

EXAMPLE 54

3-(3-bromophenyl)-1-methyl-5-(2-methylphenyl)-4(1H)-pyridone, mass spectroscopy MI, 353, yield 2%.

EXAMPLE 55

3-(3-bromophenyl)-5-(2-chlorophenyl)-1-methyl-4(1H)-pyridone, m.p. 177°–179° C., yield 10%.

EXAMPLE 56

3-(2-bromophenyl)-1-methyl-5-(3-trifluoromethylphenyl)-4(1H)-pyridone, m.p. 197°–199° C., yield 15%.

EXAMPLE 57

3-(2,3-dimethoxyphenyl)-1-methyl-5-(3-trifluoromethylphenyl)-4(1H)-pyridone, m.p. 153°–155° C., yield 20%.

EXAMPLE 58

3-(2-methoxyphenyl)-1-methyl-5-(3-trifluoromethylphenyl)-4(1H)-pyridone, m.p. 193°–196° C., yield 10%.

EXAMPLE 59

3-(2-ethylphenyl)-1-methyl-5-(3-trifluoromethylphenyl)-4(1H)-pyridone, m.p. 123°–125° C., yield 15%.

EXAMPLE 60

3-(3-bromo-4-methylphenyl)-1-methyl-5-(3-trifluoromethylphenyl)-4(1H)-pyridone, m.p. 158°–161° C., yield 30%.

EXAMPLE 61

3-(3-ethoxy-4-methoxyphenyl)-1-methyl-5-(3-trifluoromethylphenyl)-4(1H)-pyridone, mass spectroscopy MI, 403, yield 10%.

The following example demonstrates the synthesis process starting from a carbonyl halide. The corresponding enaminoketone is first formed by reaction with an enamine, the enaminoketone is amino-formylated, and the pyridone is formed by exchange with an amine.

EXAMPLE 62

3-(4-chloro-3-trifluoromethylphenyl)-1-methyl-5-phenyl-4(1H)-pyridone

To a mixture of 1.75 g. of diethylstyrylamine, 0.8 g. of pyridine and 25 ml. of diethyl ether at 0° C. was added 2.56 g. of 4-chloro-3-trifluromethylphenylacetyl chloride in 25 ml. of diethyl ether. The mixture was stirred overnight at ambient temperature, filtered and evaporated to dryness under vacuum. The residue was taken up in dichloromethane, and was washed with water and saturated sodium chloride solution and dried over magnesium sulfate. Analysis by nuclear magnetic resonance analysis showed that the product was substantially 1-diethylamino-4-(4-chloro-3-trifluoromethylphenyl)-2-phenyl-1-butene-3-one. The residue was added to 25 ml. of dimethylformamide dimethyl acetal, and refluxed for four hours. The mixture was then evaporated under vacuum to a dark oily residue, which was taken up in 50 ml. of denatured ethanol and combined with 5 g. of methylamine hydrochloride. The mixture was then refluxed for 12 hours, and was evaporated under vacuum. The residue was taken up in dichloromethane, and the solution was washed with water and saturated sodium chloride solution and dried over magnesium sulfate. The dry solution was then evaporated under vacuum to an oil, which was purified by chromatography over silica gel, eluting with benzene followed by 90 percent benzene/10 percent ethyl acetate. The product-containing fractions were combined, evaporated to dryness and recrystallized from diisopropyl ether-dichloromethane to obtain 600 mg. of 3-(4-chloro-3-trifluoromethylphenyl)-1-methyl-5-phenyl-4(1H)-pyridone, m.p. 154°–155° C.

The following exemplary compounds were prepared according to the general process of Example 62 above.

EXAMPLE 63

1,3-dimethyl-5-(3-trifluoromethylphenyl)-4(1H)-pyridone, m.p. 130°–131° C., yield 12%.

EXAMPLE 64

3-(3-chlorophenyl)-1,5-dimethyl-4(1H)-pyridone, m.p. 143°–143.5° C., yield 6%.

EXAMPLE 65

3-ethyl-1-methyl-5-(3-trifluoromethylphenyl)-4(1H)-pyridone, m.p. 95.5°–96.5° C., yield 7%.

EXAMPLE 66

3-cyclohexyl-1-methyl-5-(3-trifluoromethylphenyl)-4(1H)-pyridone, m.p. 174°–175° C., yield 40%.

EXAMPLE 67

3-isopropyl-1-methyl-5-(3-trifluoromethylphenyl)-4(1H)-pyridone, m.p. 98.5°–99.5° C., yield 10%.

EXAMPLE 68

3-hexyl-1-methyl-5-(3-trifluoromethylphenyl)-4(1H)-pyridone, m.p. 89.5°–90.5° C., yield 7%.

EXAMPLE 69

3-benzyl-1-methyl-5-(3-trifluoromethylphenyl)-4(1H)-pyridone, m.p. 98°–100° C., yield 18%.

EXAMPLE 70

3-butyl-1-methyl-5-(3-trifluoromethylphenyl)-4(1H)-pyridone, m.p. 82.5°–84° C., yield 9%.

EXAMPLE 71

3-(3-cyclohexenyl)-1-methyl-5-(3-trifluoromethylphenyl)-4(1H)-pyridone, m.p. 194°–195° C., yield 43%.

EXAMPLE 72

1-methyl-3-propyl-5-(3-trifluoromethylphenyl)-4(1H)-pyridone, m.p. 45°–47° C., yield 3%.

EXAMPLE 73

3,5-bis(3,4-dimethoxyphenyl)-1-methyl-4(1H)-pyridone, m.p. 182°–184° C., yield 1%.

EXAMPLE 74

3-(3,4-dimethoxyphenyl)-1-methyl-5-phenyl-4(1H)-pyridone, m.p. 154°–157° C., yield 4%.

EXAMPLE 75

3-(3,4-dibromocyclohexyl)-1-methyl-5-(3-trifluoromethylphenyl)-4(1H)-pyridone, hydrobromide, m.p. 196°–198° C., yield 26%, made by bromination of the corresponding 3-(3-cyclohexenyl) compound.

EXAMPLE 76

3-(3-isopropenylphenyl)-1-methyl-5-phenyl-4(1H)-pyridone, NMR peaks at 125, 214, 302 and 327 CPS; aromatic protons at 420–470 CPS; yield 4%.

EXAMPLE 77

3-(3-ethylphenyl)-1-methyl-5-phenyl-4(1H)-pyridone, m.p. 135°–137° C., yield 5%.

EXAMPLE 78

3-(3-cyclohexylmethylphenyl)-1-methyl-5-phenyl-4(1H)-pyridone, m.p. 147°–148° C., yield 9%.

EXAMPLE 79

3-(4-methoxy-3-methylphenyl)-1-methyl-5-phenyl-4(1H)-pyridone, m.p. 157°–160° C., yield 2.5%.

EXAMPLE 80

3-(3-bromo-4-methylphenyl)-1-methyl-5-phenyl-4(1H)-pyridone, m.p. 168°–170° C., yield 13%.

EXAMPLE 81

1-methyl-3-(3-nitrophenyl)-5-(3-trifluoromethylphenyl)-4(1H)-pyridone, m.p. 209°–211° C., yield 51%.

EXAMPLE 82

1-methyl-3-phenyl-5-(3-phenylthiophenyl)-4(1H)-pyridone, mass spectrometry MI, 369, yield 8%.

EXAMPLE 83

3-(3,4-dimethylphenyl)-1-methyl-5-phenyl-4(1H)-pyridone, m.p. 108°–111° C., yield 5%.

EXAMPLE 84

3-(3,5-dimethylphenyl)-1-methyl-5-phenyl-4(1H)-pyridone, m.p. 148°–150° C., yield 10%.

EXAMPLE 85

3-(3-butylphenyl)-1-methyl-5-phenyl-4(1H)-pyridone, m.p. 87°–89° C., yield 6%.

EXAMPLE 86

3-(2,5-dimethylphenyl)-1-methyl-5-phenyl-4(1H)-pyridone, m.p. 188°–190° C., yield 4%.

EXAMPLE 87

1-methyl-3-phenoxy-5-(3-trifluoromethylphenyl)-4(1H)-pyridone, m.p. 144°–145° C., yield 15%.

EXAMPLE 88

3-ethoxycarbonyl-1-methyl-5-(3-trifluoromethylphenyl)-4(1H)-pyridone, m.p. 151°–152° C., yield 62%.

EXAMPLE 89

1-methyl-3-(3-trifluoromethylphenyl)-5-phenylthio-4(1H)-pyridone, m.p. 164°-165° C., yield 18%.

EXAMPLE 90

3-(2,4-dichlorophenoxy)-1-methyl-5-(3-trifluoromethylphenyl)-4(1H)-pyridone, m.p. 129°-130° C., yield 40%.

EXAMPLE 91

3-ethylthio-1-methyl-5-(3-trifluoromethylphenyl)-4(1)-pyridone, m.p. 84°-85° C., yield 40%.

The following compound was prepared by oxidizing the compound of Example 91 with sodium periodate in aqueous ethanol at room temperature for 16 hours.

EXAMPLE 92

3-ethylsulfinyl-1-methyl-5-(3-trifluoromethylphenyl)-4(1H)-pyridone, m.p. 146°-148° C., yield 82%.

The following compounds were also made by the process of Example 62.

EXAMPLE 93

3-(5-bromo-2-fluorophenyl)-1-methyl-5-phenyl-4(1H)-pyridone, m.p. 148°-150° C., yield 6%.

EXAMPLE 94

1-methyl-3-(5-nitro-2-methylphenyl)-5-phenyl-4(1H)-pyridone, m.p. 185°-187° C., yield 5%.

EXAMPLE 95

1-methyl-3-propylthio-5(3-trifluoromethylphenyl)-4(1H)-pyridone, m.p. 101°-102° C., yield 25%.

EXAMPLE 96

1-methyl-3-methylthio-5-(3-trifluoromethylphenyl)-4(1H)-pyridone, m.p. 121°-122° C., yield 20%.

EXAMPLE 97

1-methyl-3-(3-trifluoromethylphenyl)-5-(4-trifluoromethylphenyl)-4(1H)-pyridone, m.p. 110°-113° C., yield 10%.

EXAMPLE 98

1-methyl-3-(3-trifluoromethylphenyl)-5-trifluoromethylthio-4(1H)-pyridone, m.p. 122°-124° C., yield 21%.

EXAMPLE 99

3-(3,4-dimethoxyphenyl)-1-methyl-5-(3-trifluoromethylphenyl)-4(1H)-pyridone, m.p. 148°-150° C., yield 10%.

EXAMPLE 100

Mixture of 3-(5-fluoro-2-iodophenyl)-1-methyl-5-phenyl-4(1H)-pyridone and 3-(2-bromo-5-fluorophenyl)-1-methyl-5-phenyl-4(1H)-pyridone, mixed m.p. 211°-214° C., yield 7%.

EXAMPLE 101

3-benzylthio-1-methyl-5-(3-trifluoromethylphenyl)-4(1H)-pyridone, m.p. 121°-122° C., yield 40%.

EXAMPLE 102

3-(4-benzyloxyphenyl)-1-methyl-5-(3-trifluoromethylphenyl)-4(1H)-pyridone, amorphous, yield 10%.

The compound below was prepared by the hydrogenation of Example 102 in acetic acid in the presence of 5% palladium on carbon hydrogenation catalyst.

EXAMPLE 103

3-(4-hydroxyphenyl)-1-methyl-5-(3-trifluoromethylphenyl)-4(1H)-pyridone, m.p. 162°-163° C., yield 50%.

The general process of Example 62 was used to prepare the compounds below.

EXAMPLE 104

3-(4-chloro-3-trifluoromethylphenyl)-5-ethoxy-1-methyl-4(1H)-pyridone, m.p. 158°-159° C., yield 15%.

EXAMPLE 105

1-methyl-3-isopropylthio-5-(3-trifluoromethylphenyl)-4(1H)-pyridone, m.p. 93°-94° C., yield 32%.

EXAMPLE 106

3-(4-chloro-3-trifluoromethylphenyl)-5-ethylthio-1-methyl-4(1H)-pyridone, m.p. 115°-116° C., yield 11%.

EXAMPLE 107

3-(2,5-dimethylphenyl)-1-methyl-5-(3-trifluoromethylphenyl)-4(1H)-pyridone, m.p. 165°-167° C., yield 2%.

EXAMPLE 108

3-(3,5-dimethylphenyl)-1-methyl-5-(3-trifluoromethylphenyl)-4(1H)-pyridone, m.p. 160°-163° C., yield 6%.

EXAMPLE 109

3-(2,4-dichlorophenyl)-1-methyl-5-(3-trifluoromethylphenyl)-4(1H)-pyridone, m.p. 139°-142° C., yield 11%.

EXAMPLE 110

1-methyl-3-(2-trifluoromethylphenyl)-5-(3-trifluoromethylphenyl)-4(1H)-pyridone, m.p. 135°-138° C., yield 24%.

EXAMPLE 111

3-(3,4-dimethylphenyl)-1-methyl-5-(3-trifluoromethylphenyl)-4-(1H)-pyridone, m.p. 150°-153° C., yield 15%.

EXAMPLE 112

3-(3-iodophenyl)-1-methyl-5-(3-trifluoromethylphenyl)-4(1H)-pyridone, m.p. 178°-181° C., yield 15%.

EXAMPLE 113

3-ethyl-1-methyl-5-(3-methoxyphenyl)-4(1H)-pyridone, yield 5%, mass spectroscopy MI, 243.

EXAMPLE 114

1-methyl-3-(3-iodophenyl)-5-phenyl-4(1H)-pyridone, m.p. 190°-193° C., yield 8%.

EXAMPLE 115

1-methyl-3-(4-methoxyphenoxy)-5-(3-trifluoromethylphenyl)-4(1H)-pyridone, m.p. 119°-120° C., yield 25%.

EXAMPLE 116

1-methyl-3-(2-chloro-4-fluorophenyl)-5-(3-trifluoromethylphenyl)-4(1H)-pyridone, m.p. 183°-186° C., yield 20%.

EXAMPLE 117

1-methyl-3-(4-chloro-3-trifluoromethylphenyl)-5-trifluoromethyl-4(1H)-pyridone, m.p. 164°–165° C., yield 2%.

EXAMPLE 118

1-methyl-3-(4-chloro-3-trifluoromethylphenyl)-5-propyl-4(1H)-pyridone, m.p. 141°–142° C., yield 8%.

EXAMPLE 119

1-methyl-3-isopropylthio-5-(4-chloro-3-trifluoromethylphenyl)-4(1H)-pyridone, m.p. 127°–129° C., yield 15%.

EXAMPLE 120

1-methyl-3-(4-chloro-3-trifluoromethylphenyl)-5-propylthio-4(1H)-pyridone, m.p. 128°–130° C., yield 15%.

EXAMPLE 121

3-ethyl-1-methyl-5-(4-chloro-3-trifluoromethylphenyl)-4(1H)-pyridone, m.p. 121°–123° C., yield 1%.

EXAMPLE 122

1-methyl-3-(2,4-dimethylphenyl)-5-(3-trifluoromethylphenyl)-4(1H)-pyridone, m.p. 128°–131° C., yield 6%.

EXAMPLE 123

3-isopropoxy-1-methyl-5-(3-trifluoromethylphenyl)-4(1H)-pyridone, mass spectroscopy MI, 311, yield 1%.

EXAMPLE 124

1-methyl-3-(4-chlorophenoxy)-5-(3-trifluoromethylphenyl)-4(1H)-pyridone, m.p. 90°–91° C., yield 15%.

EXAMPLE 125

1-methyl-3-(3-methylthiophenyl)-5-(3-trifluoromethylphenyl)-4(1H)-pyridone, m.p. 150°–153° C., yield 25%.

EXAMPLE 126

3-(2,3-dichlorophenoxy)-1-methyl-5-(3-trifluoromethylphenyl)-4(1H)-pyridone, m.p. 200°–202° C., yield 30%.

EXAMPLE 127

3-(3,5-dichlorophenoxy)-1-methyl-5-(3-trifluoromethylphenyl)-4(1H)-pyridone, m.p. 128°–130° C., yield 30%.

EXAMPLE 128

3-(3,4-dichlorophenoxy)-1-methyl-5-(3-trifluoromethylphenyl)-4(1H)-pyridone, m.p. 127°–129° C., yield 20%.

EXAMPLE 129

3-(4-chloro-3-trifluoromethylphenyl)-1-methyl-5-isopropyl-4(1H)-pyridone, m.p. 85°–87° C., yield 25%.

EXAMPLE 130

3-(2,5-dichlorophenoxy)-1-methyl-5-(3-trifluoromethylphenyl)-4(1H)-pyridone, m.p. 162°–164° C., yield 28%.

EXAMPLE 131

1-methyl-3-(3-trifluoromethylphenyl)-5-(3-trifluoromethylthiophenyl)-4(1H)-pyridone, a glass, yield 1%.

EXAMPLE 132

1-methyl-3-(2,2,2-trifluoroethoxy)-5-(3-trifluoromethylphenyl)-4(1H)-pyridone, m.p. 97°–99° C., yield 1%.

EXAMPLE 133

3-(4-chloro-3-trifluoromethylphenyl)-1-methyl-5-(3-trifluoromethylthiophenyl)-4(1H)-pyridone, m.p. 90°–92° C., yield 18%.

The next example illustrates a synthesis similar to the synthesis of Example 62 except that the enaminoketone is reacted first with an amine, and then with an aminoformylating agent to form the desired pyridone.

EXAMPLE 134

1-methyl-3-(3-methylthiophenyl)-5-phenyl-4(1H)-pyridone

An enaminoketon was made according to the procedure of the first step of Example 62 above, starting with 17.5 g. of N,N-diethylstyrylamine and 15 g. of (3-methylthiophenyl)acetyl chloride. The enaminoketone was dissolved in 300 ml. of ethanol, mixed with 20 g. of methylamine hydrochloride and stirred for about 60 hours. The solvent was then evaporated, the residue was extracted with ethyl ether, and the solution was washed with water. The organic layer was dried over anhydrous sodium sulfate, and the dried solution was evaporated to dryness.

The residue was mixed with 50 ml. of dimethylformamide dimethyl acetal and heated at reflux temperature for 20 hours. The reaction mixture was then poured into water, and the mixture was extracted first with ether and then with methylene chloride. Both extracts were washed with water, dried and evaporated to dryness. The product was 9 g. of 1-methyl-3-(3-methylthiophenyl)-5-phenyl-4(1H)-pyridone, which was identified by NMR, which showed peaks at 144 and 227 CPS, with aromatic protons at 420–440 and 442–458 CPS.

By a similar process, the following compounds were also produced. Example 135 was produced by oxidation of the compound of Example 134 with m-chloroperbenzoic acid.

EXAMPLE 135

1-methyl-3-(3-methylsulfinylphenyl)-5-phenyl-4(1H)-pyridone, m.p. 161°–164° C., yield 57%.

EXAMPLE 136

3-ethylthio-1-methyl-5-(2-chloro-5-trifluoromethylphenyl)-4(1H)-pyridone, m.p. 127°–129° C., yield 10%.

EXAMPLE 137

3-(2-chloro-5-trifluoromethylphenyl)-1-methyl-5-phenyl-4(1H)-pyridone, m.p. 150°–152° C., yield 25%.

EXAMPLE 138

3-(2-chloro-5-trifluoromethylphenyl)-1-methyl-5-(3-trifluoromethylphenyl)-4(1H)-pyridone, yield 25%.

The following example illustrates a variation of the process beginning with a carbonyl halide, wherein the enaminoketone is first exchanged with an amine, and the pyridone is then formed by formylation of the intermediate.

EXAMPLE 139

3-(3-benzyloxyphenyl)-1-methyl-5-phenyl-4(1H)-pyridone

An enaminoketone was prepared, following the first step of the procedure of Example 62 above, from 14.4 g. of (3-benzyloxyphenyl)acetyl chloride and 9.6 g. of N,N-diethylstyrylamine. A 13 g. portion of the enaminoketone was dissolved in 100 ml. of methanol and 26 g. of methylamine hydrochloride was added. The reaction mixture was heated at reflux temperature overnight. The solvent was removed under vacuum, 100 ml. of water was added, and the mixture was then extacted with methylene chloride. The extract was washed with dilute hydrochloric acid and then with water, and the organic layer was separated, dried, filtered and evaporated to dryness. The resulting intermediate, 4-(3-benzyloxyphenyl)-1-methylamino-2-phenyl-1-buten-3-one, was dissolved in 125 ml. of ethyl ether.

The solution was cooled to 5° C., and 12 g. of sodium methoxide was added. While the reaction mixture was held at about 5° C., 50 ml. of ethyl formate was added slowly. The mixture was then stirred as it was allowed to warm slowly to room temperature. The reaction mixture was then evaporated to dryness, the residue was extracted with chloroform, and the extract was washed with water and dried. The product was purified by chromatography over silica gel with a 50:50 mixture of ethyl acetate:hexane. The product-containing fractions were collected, combined, and evaporated to dryness. The product was recrystallized from ethyl acetate to produce 1.5 g. of 3-(3-benzyloxyphenyl)-1-methyl-5-phenyl-4(1H)-pyridone, m.p. 158°-160° C.

The following exemplary compounds were also produced according to the process of Example 139 above.

EXAMPLE 140

3-(3-isobutylphenyl)-1-methyl-5-phenyl-4(1H)-pyridone, NMR doublets at 54 and 147 CPS; a septet at 113 CPS; aromatic protons at 420°-460 CPS.

EXAMPLE 141

1-methyl-3-(3-nitrophenyl)-5-phenyl-4(1H)-pyridone, m.p. 135°-136.5° C., yield 33%.

EXAMPLE 142

1-methyl-3-allylthio-5-(3-trifluoromethylphenyl)-4(1H)-pyridone, m.p. 74°-75° C., yield 5%.

EXAMPLE 143

3-(4-chloro-3-trifluoromethylphenyl)-1-methyl-5-phenoxy-4(1H)-pyridone, m.p. 130°-131° C., yield 27%.

The next example illustrates a process similar to that above, but wherein the enaminoketone is first formylated and then exchanged with the amine to form the pyridone.

EXAMPLE 144

3-ethoxy-1-methyl-5-(3-trifluoromethylphenyl)-4(1H)-pyridone

An enaminoketone was formed from 4.86 g. of N,N-diethyl-3-trifluoromethylstyrylamine and 2.44 g. of ethoxyacetyl chloride in the presence of 1.6 g. of pyridine. The desired enaminoketone, 1-diethylamino-4-ethoxy-2-(3-trifluoromethylphenyl)-1-buten-3-one was formed. To the unpurified enaminoketone in 75 ml. of anhydrous tetrahydrofuran at 0° C. was added 3.2 g. of sodium methoxide, and the mixture was stirred for 15 minutes. To this mixture was added 4.4 g. of ethyl formate dropwise. The mixture was stirred for three hours, and 50 ml. of a 40 percent methylamine solution in water was added followed by 5 g. of methylamine hydrochloride. The reaction mixture was stirred overnight at ambient temperature, and was then evaporated to dryness under vacuum. The residue was taken up in dichloromethane, and the solution was washed with water and dried over magnesium sulfate. The dry solution was filtered, and evaporated under vacuum to obtain a dark residue which was triturated in cold diisopropyl ether. The solids were removed by filtration and recrystallized from diisopropyl etherdichloromethane to obtain 1.6 g. of 3-ethoxy-1-methyl-5-(3-trifluoromethylthylphenyl)-4(1H)-pyridone, m.p. 131°-133° C.

The following examples illustrate the preparation of 3-hydroxyphenyl-substituted compounds, from which other substituted compounds are prepared in the next examples following.

EXAMPLE 145

3-(3-hydroxyphenyl)-1-methyl-5-phenyl-4(1H)-pyridone

A 1 g. portion of the product of Example 139 was dissolved in 250 ml. of acetic acid, and 1 g. of 5% palladium on carbon was added. The mixture was hydrogenated for about 45 minutes, filtered, and the filtrate was evaporated to dryness. The product was recrystallized from ethyl acetate-hexane to produce 0.45 g. of 3-(3-hydroxyphenyl)-1-methyl-5-phenyl-4(1H)-pyridone, m.p. 223°-225° C.

The same compound was also made by a cleavage with pyridine hydrochloride as follows.

A 2 g. portion of 3-(3-methoxyphenyl)-1-methyl-5-phenyl-4(1H)-pyridone was mixed with 15 g. of pyridine hydrochloride and the mixture was heated at reflux temperature for about 1 hour. The mixture was then poured into a large amount of water, and the precipitated solids were separated by filtration. The solids were then recrystallized from ethanol-ethyl ether to yield 1.1 g. of 3-(3-hydroxyphenyl)-1-methyl-5-phenyl-4(1H)-pyridone. An additional 0.65 g. was recovered by concentration of the filtrate above. The product was identical to that of the above example.

The following compound was made by a process similar to Example 145.

EXAMPLE 146

3-cyclohexyl-5-(3-hydroxyphenyl)-1-methyl-4(1H)-pyridone, m.p. 155°-165° C., yield 13%.

EXAMPLE 147

3-(3-ethoxyphenyl)-1-methyl-5-phenyl-4(1H)-pyridone

A 3.2 g. portion of the product of Example 145 was added to a suspension of 0.86 g. of sodium hydride in 50 ml. of dimethylsulfoxide. The mixture was stirred at room temperature, and 3.5 g. of ethyl iodide was added. The mixture was stirred for two and one-half hours more, and extracted with ethyl acetate. The extract was washed with dilute hydrochloric acid and then with water, and dried. The dried extract was then filtered and concentrated to dryness under vacuum. The product was 2.2 g. of 3-(3-ethoxyphenyl)-1-methyl-5-phenyl-4(1H)-pyridone, m.p. 133°-135° C.

The exemplary compounds below were prepared according to methods similar to that of Example 147.

EXAMPLE 148

3-(3-isopropoxyphenyl)-1-methyl-5-phenyl-4(1H)-pyridone, NMR peaks at 81, 209 and 276 CPS; aromatic protons at 401–468 CPS; yield 18%.

EXAMPLE 149

1-methyl-3-phenyl-5-[3-(1,1,2,2-tetrafluoroethoxy)phenyl]-4(1H)-pyridone, m.p. 119°–121° C., yield 84%, made by using tetrafluoroethylene, in the presence of potassium hydroxide.

EXAMPLE 150

3-(3-acetoxyphenyl)-1-methyl-5-phenyl-4(1H)-pyridone, NMR peaks at 134 and 210 CPS; aromatic protons at 415–466 CPS; yield 28%, made by using acetic anhydride in the presence of sulfuric acid.

EXAMPLE 151

1-methyl-3-phenyl-5-(3-propoxyphenyl)-4(1H)-pyridone, NMR peaks at 54, 101.5, 208 and 232 CPS; aromatic protons at 400–463 CPS; yield 31%.

EXAMPLE 152

3-(3-cyclohexylmethoxyphenyl)-1-methyl-5-phenyl-4(1H)-pyridone, NMR peaks at 214 and 226 CPS; a broad peak at 35–124 CPS; aromatic protons at 402–466 CPS; yield 16%.

EXAMPLE 153

1-methyl-3-(3-phenoxyphenyl)-5-phenyl-4(1H)-pyridone, NMR peak at 214 CPS; aromatic protons at 410–470 CPS; yield 34%.

The examples below illustrate the preparation of pyridinethiones.

EXAMPLE 154

1-methyl-3-propyl-5-(3-trifluoromethylphenyl)-4(1H)-pyridinethione

A 2.0 g. portion of 1-methyl-3-propyl-5-(3-trifluoromethylphenyl)-4(1H)-pyridone was mixed with a 2.0 g. portion of phosphorus pentasulfide in 100 ml. of pyridine, and the mixture was heated at reflux for two hours. The mixture was then cooled, poured into a large excess of water, and filtered. The solids were recovered by filtration and drystallized from ethanol to obtain 0.9 g. of 1-methyl-3-propyl-5-(3-trifluoromethylphenyl)-4(1H)-pyridinethione, m.p. 145°–148° C.

EXAMPLE 155

3,5-bis(3-chlorophenyl)-1-methyl-4(1H)-pyridinethione, m.p. 210°–212° C., yield 86%.

EXAMPLE 156

3-(3-chlorophenyl)-1-methyl-5-phenyl-4(1H)-pyridinethione, m.p. 190°–193° C., yield 71%.

EXAMPLE 157

1-methyl-3-phenyl-5-(3-trifluoromethylphenyl)-4(1H)-pyridinethione, m.p. 210° C., yield 70%.

EXAMPLE 158

3-(3-bromophenyl)-1-methyl-5-phenyl-4(1H)-pyridinethione, m.p. 185°–188° C., yield 59%.

EXAMPLE 159

1-methyl-3-(4-chlorophenyl)-5-(3-trifluoromethylphenyl)-4(1H)-pyridinethione, m.p. 239°–242° C., yield 25%.

EXAMPLE 160

1-methyl-3-(3-methylphenyl)-5-(3-trifluoromethylphenyl)-4(1H)-pyridinethione, m.p. 193°–196° C., yield 50%.

EXAMPLE 161

1-methyl-3-(2-methylphenyl)-5-(3-trifluoromethylphenyl)-4(1H)-pyridinethione, m.p. 193°–195° C., yield 35%.

EXAMPLE 162

1-methyl-3-phenoxy-5-(3-trifluoromethylphenyl)-4(1H)-pyridinethione, m.p. 127°–131° C., yield 40%.

EXAMPLE 163

3-ethylthio-1-methyl-5-(3-trifluoromethylphenyl)-4(1H)-pyridinethione, m.p. 136°–138° C., yield 55%.

EXAMPLE 164

3-ethoxy-1-methyl-5-(3-trifluoromethylphenyl)-4(1H)-pyridinethione, m.p. 153°–155° C., yield 5%.

The compounds described above have been tested against aquatic weeds and algae to determine the range of their efficacy. The outstanding results produced by the compounds in the representative tests reported below are exemplary of the outstanding activity of the compounds.

Blank spaces in the tables below indicate that the compound was not tested against the named species. In many instances, a given compound has been tested repeatedly against a plant species. In these instances, a single representative result is usually reported; in some cases, multiple results have been averaged.

Untreated control weeds or algae were included in all tests. Ratings of the control produced by the compounds were made by comparison of the treated weeds or algae with the untreated controls.

The various rating scales used in the tests are explained in the descriptions which follow.

Test 1

Test Against Aquatic Weeds

The aquatic weeds against which the compounds were evaluated in this test were coontail, *Ceratophyllum demersum*, L.; hydrilla, *Hydrilla verticillata* (L.F.); and duckweed, *Lemna minor* L. The weeds are prepared by cutting 10-cm. terminal sprigs of coontail and hydrilla, and selecting approximately enough duckweed to cover the surface of the water in a 10-ml. beaker. The weeds were then placed in plastic cartons containing 785 ml. of dechlorinated water containing the compound.

The compounds for this test were formulated as follows. Twenty mg. of compound was weighed into a vial. To the compound was added 1 ml. of acetone, followed by 9 ml. of aqueous 0.1 percent polyoxyethylene sorbitan monooleate solution. A 4 ml. aliquot of the aqueous solution or dispersion of the compound was then pipetted into a plastic carton to obtain a 10 parts per million by weight (ppm) concentration of the test compound. The cartons were covered with plastic lids and placed on tables at about 24°–25° C., in a room where the illumination was at the level of about 70–100 foot candles.

Observations of the efficacy of the compounds were made 7 days after treatment. The effects were rated on a 1–5 scale, where 1 indicates no effect, and 5 indicates complete kill of the weeds. It must be pointed out, however, that the 7-day period is hardly long enough for the full effect of these compounds to become observable, because of the slow action of them. Accordingly, a rating of 2 or 3 in these tests is an indication of good activity.

Test 2

Test against typical algae

The compounds were tested against three species of algae at the same concentration used in Test 1, 10 ppm. The algae used in this test were *Chlorella vulgaris, Scenedesmus quadricauda,* and *Anacystis nidulans.* Cultures of these three algae are grown on artificial media. Cultures were used in these tests when they were from 3 to 7 days old. The algae cultures were diluted for use in these tests by adding 5 ml. of Anacystis culture, or 1 ml. of Chlorella or Scenedesmus culture, to 500 ml. of sterile growth medium. In some instances, 2 ml. of inoculated medium were used in each test, and in some instances, the volume is 10 ml.

The compounds are formulated as described in Test 1, and a sufficient amount of formulated compound is added to each portion of algae-inoculated medium to provide a concentration of 10 ppm of the compound.

The treated and untreated control algae cultures are stored as described in test 1, and are observed after 7 days. Algicidal effects of the compounds are rated on the 1–5 scale, where 1 indicates no effect and 5 indicates death of the algae.

In some instances, algicidal tests were carried out only at rates other than 10 ppm. In these instances, the rate is indicated in table 1 below in parenthesis next to the example number of the compound.

TABLE 1

| Compound of Example No. | Hyd-rilla | Coon-tail | Duck-weed | Chlo-rella | Scene-desmus | Ana-cystis |
|---|---|---|---|---|---|---|
| 1 | 2 | 2 | 2 | 4 | 5 | 5 |
| 3 | 1 | 1 | 1 | 4 | 3 | 3 |
| 5 | 1 | 1 | 1 | 4 | 3 | 3 |
| 6 | 1 | 1 | 1 | | | |
| 6 (0.5) | | | | 3 | 5 | 3 |
| 10 (0.5) | | | | 3 | 3 | 4 |
| 11 (0.5) | | | | 5 | 5 | 3 |
| 12 (0.5) | | | | 3 | 3 | 4 |
| 13 | 2 | 2 | 2 | 4 | 3 | 3 |
| 14 | 2 | 2 | 2 | 5 | 5 | 5 |
| 15 | 2 | 2 | 2 | 4 | 5 | 5 |
| 16 | 2 | 2 | 2 | 4 | 5 | 5 |
| 17 | 1 | 1 | 1 | 3 | 5 | 5 |
| 18 | 2 | 2 | 2 | 4 | 4 | 4 |
| 19 | 1 | 2 | 2 | 4 | 4 | 4 |
| 20 | 1 | 2 | 2 | 4 | 3 | 4 |
| 21 | 2 | 2 | 1 | 4 | 3 | 4 |
| 22 | 1 | 2 | 3 | | | |
| 22 (0.5) | | | | 4 | 5 | 4 |
| 23 | 2 | 1 | 2 | | | |
| 24 | 2 | 2 | 2 | | | |
| 25 | 2 | 2 | 2 | 4 | 3 | 3 |
| 26 | 2 | 2 | 2 | 5 | 5 | 5 |
| 29 | 1 | 1 | 1 | 4 | 4 | 3 |
| 30 (.5) | | | | 3 | 3 | 4 |
| 32 (.5) | | | | 5 | 5 | 3 |
| 33 | 3 | 3 | 3 | | | |
| 34 | 1 | 1 | 2 | 4 | 1 | 1 |
| 37 | 2 | 3 | 3 | 4 | 1 | 1 |
| 38 | 3 | 3 | 3 | | | |
| 39 | 1 | 1 | 1 | | | |
| 40 | 3 | 3 | 3 | 5 | 5 | 5 |
| 41 | 3 | 3 | 3 | 4 | 5 | 5 |
| 42 | 3 | 3 | 3 | | | |
| 42 (0.5) | | | | 3 | 5 | 2 |
| 43 | 3 | 3 | 3 | 1 | 4 | 5 |
| 45 | 3 | 3 | 3 | 4 | 1 | 2 |
| 46 | 3 | 3 | 2 | 3 | | 5 |
| 47 | 3 | 3 | 3 | 5 | 5 | 5 |
| 48 | 1 | 1 | 1 | 5 | 5 | 1 |
| 49 | 3 | 3 | 3 | 5 | 5 | 5 |
| 50 | 2 | 2 | 2 | 5 | 5 | 5 |
| 52 | 2 | 2 | 2 | 4 | 5 | 5 |
| 55 | 1 | 1 | 1 | 4 | 4 | 3 |
| 56 | 3 | 3 | 3 | 4 | 4 | 3 |
| 57 | 3 | 3 | 3 | 1 | 1 | 1 |
| 58 | 3 | 3 | 3 | 5 | 5 | 5 |
| 59 | 3 | 3 | 3 | 4 | 5 | 1 |
| 60 | 1 | 1 | 1 | 4 | 3 | 3 |
| 63 | 2 | 2 | 2 | | | |
| 63 (0.5) | | | | 3 | 3 | 4 |
| 65 | 2 | 2 | 2 | 5 | 5 | 5 |
| 66 | 1 | 2 | 2 | 3 | 5 | 5 |
| 67 | 2 | 2 | 2 | | | |
| 69 | 1 | 1 | 1 | 3 | 5 | 5 |
| 70 | 1 | 1 | 4 | | | |
| 71 | 1 | 1 | 1 | | | |
| 78 | 3 | 3 | 3 | 5 | 5 | 5 |
| 79 | 2 | 2 | 3 | 3 | 5 | 5 |
| 80 | 1 | 3 | 1 | 4 | 2 | 3 |
| 81 | 3 | 4 | 3 | 4 | 2 | 3 |
| 82 | 3 | 2 | 3 | 5 | 5 | 5 |
| 84 | 1 | 1 | 3 | 5 | 5 | 5 |
| 85 | 1 | 1 | 4 | | | |
| 86 | 1 | 1 | 1 | | | |
| 87 | 2 | 3 | 3 | 5 | 5 | 5 |
| 90 | 3 | 3 | 3 | 5 | 5 | 5 |
| 91 | 3 | 3 | 3 | 5 | 5 | 5 |
| 92 | 3 | 3 | 3 | 3 | 5 | 5 |
| 95 | 3 | 3 | 3 | 4 | 3 | 4 |
| 96 | 3 | 3 | 3 | 4 | 5 | 5 |
| 97 | 2 | 1 | 2 | 5 | 5 | 5 |
| 98 | 3 | 3 | 3 | 4 | 3 | 2 |
| 99 | 3 | 3 | 2 | 1 | 5 | 5 |
| 103 | 3 | 3 | 2 | 3 | 5 | 5 |
| 105 | 3 | 3 | 3 | 5 | 5 | 5 |
| 106 | 3 | 3 | 3 | 5 | 5 | 5 |
| 108 | 3 | 3 | 3 | 5 | 5 | 5 |
| 109 | 3 | 3 | 3 | 4 | 3 | 3 |
| 110 | 2 | 1 | 3 | 4 | 3 | 3 |
| 111 | 1 | 1 | 3 | 5 | | 5 |
| 112 | 3 | 2 | 3 | 4 | 5 | 5 |
| 114 | 3 | 3 | 3 | 4 | | 5 |
| 116 | 2 | 2 | 2 | 5 | 4 | 5 |
| 119 | 3 | 3 | 3 | 4 | 1 | 2 |
| 120 | 3 | 3 | 3 | 5 | 5 | 4 |
| 122 | 3 | 3 | 3 | 5 | 1 | 5 |
| 125 | 2 | 2 | 2 | 4 | 3 | 3 |
| 126 | 3 | 3 | 3 | 4 | 3 | 3 |
| 127 | 3 | 3 | 3 | 4 | 1 | 4 |
| 128 | 3 | 3 | 3 | 5 | 5 | 5 |
| 129 | 3 | 3 | 3 | 4 | 3 | 3 |
| 130 | 3 | 3 | 3 | 4 | 4 | 3 |
| 131 | 3 | 3 | 3 | 5 | 5 | 5 |
| 132 | | | | 5 | 5 | 5 |
| 133 | 3 | 3 | 1 | 5 | 5 | 1 |
| 135 | 1 | 1 | 1 | | | |
| 136 | 3 | 3 | 3 | 5 | 5 | 1 |
| 137 | 3 | 3 | 3 | 4 | 5 | 5 |
| 138 | 3 | 3 | 3 | 5 | 5 | 5 |
| 140 | 3 | 3 | 3 | 5 | 5 | 5 |
| 141 | 2 | 2 | 1 | 1 | 1 | 1 |
| 143 | 3 | 3 | 3 | 4 | 3 | 4 |
| 144 | 3 | 3 | 2 | 2 | 5 | 5 |
| 145 | 1 | 1 | 1 | 3 | 3 | 2 |
| 147 | 3 | 3 | 3 | 5 | 5 | 5 |
| 148 (0.5) | | | | 3 | 5 | 3 |
| 149 | 3 | 3 | 5 | | | |
| 149 (0.5) | | | | 4 | 5 | 4 |
| 155 | 2 | 2 | 1 | | | |

TABLE 1-continued

| Compound of Example No. | Hydrilla | Coontail | Duckweed | Chlorella | Scenedesmus | Anacystis |
|---|---|---|---|---|---|---|
| 156 | 2 | 2 | 2 | | | |
| 157 | 2 | 2 | 2 | | | |
| 158 | 3 | 3 | 3 | 5 | 5 | 5 |
| 159 | 2 | 2 | 2 | 2 | 5 | 5 |
| 161 | 3 | 3 | 3 | 2 | 5 | 1 |
| 162 | 1 | 1 | 1 | 1 | 5 | 4 |
| 163 | 1 | 1 | 1 | 5 | 5 | 4 |

Test 3

Test Against Aquatic Weeds

Additional tests of a number of the compounds were performed under conditions which more closely duplicated conditions to be found in the field. The test weed was hydrilla, and the tests were initiated by preparing sprigs of hydrilla as described in Test 1, and placing two sprigs in each 785-ml. portion of water. In these tests, additional nutrients were added to the water to assure that the hydrilla could grow throughout the test period. The nutrients were as follows:

| Nutrients | mg/l |
|---|---|
| $KH_2PO_4$ | 14 |
| $KNO_3$ | 50 |
| $Ca(NO_3)_2$ | 82 |
| $MgSO_4$ | 24 |
| $H_3BO_3$ | 0.3 |
| $MnCl_2 \cdot 4H_2O$ | 0.2 |
| $CuSO_4 \cdot 5H_2O$ | 0.008 |
| $H_2MoO_4 \cdot H_2O$ | 0.002 |
| Zn acetate | 0.02 |
| Chelated iron | 2 |
| $NaHCO_3$ | 50 |

The compounds were formulated as described in Test 1, and were added to the test cartons in concentrations described in the table below.

The test cartons were stored for approximately 3 weeks in a growth room at about 30° C. under light at 1100 foot candles on a cycle of 12 hours on, 12 hours off, together with untreated controls, and were then read on the same 1-5 scale that was described in Test 1 above.

Many of the compounds listed in the table below were tested two or more times on different occasions. In these instances, the data obtained from the tests at the same concentrations have been averaged.

TABLE 2

| Compound of Example No. | Concentration | Rating |
|---|---|---|
| 1 | 10 ppm | 5 |
| 1 | 0.3 | 5 |
| 1 | 0.1 | 5 |
| 1 | 0.03 | 5 |
| 3 | 0.3 | 5 |
| 3 | 0.1 | 5 |
| 3 | 0.03 | 5 |
| 5 | 10 | 5 |
| 5 | 0.3 | 5 |
| 5 | 0.1 | 5 |
| 5 | 0.03 | 4 |
| 6 | 0.3 | 5 |
| 6 | 0.1 | 5 |
| 6 | 0.03 | 1 |
| 10 | 0.3 | 5 |
| 10 | 0.1 | 3 |
| 10 | 0.03 | 1 |
| 13 | 10 | 5 |
| 13 | 0.3 | 5 |
| 13 | 0.1 | 1 |
| 13 | 0.03 | 1 |
| 14 | 0.3 | 5 |
| 14 | 0.1 | 5 |
| 14 | 0.03 | 1 |
| 16 | 0.3 | 5 |
| 16 | 0.1 | 5 |
| 16 | 0.03 | 4 |
| 18 | | |
| 65 | 0.03 | 4 |
| 66 | 5 | |
| 18 | 0.1 | 5 |
| 18 | 0.03 | 4 |
| 19 | 10 | 5 |
| 19 | 0.3 | 5 |
| 19 | 0.1 | 2 |
| 19 | 0.03 | 1 |
| 20 | 10 | 5 |
| 20 | 0.3 | 1 |
| 20 | 0.1 | 1 |
| 20 | 0.03 | 1 |
| 21 | 0.3 | 5 |
| 21 | 0.1 | 5 |
| 21 | 0.03 | 5 |
| 22 | 0.3 | 5 |
| 22 | 0.1 | 5 |
| 22 | 0.03 | 4 |
| 25 | 0.3 | 5 |
| 25 | 0.1 | 5 |
| 25 | 0.03 | 4 |
| 29 | 0.3 | 5 |
| 29 | 0.1 | 5 |
| 29 | 0.03 | 5 |
| 37 | 10 | 2 |
| 37 | 0.3 | 1 |
| 37 | 0.1 | 1 |
| 37 | 0.03 | 1 |
| 40 | 10 | 5 |
| 40 | 0.3 | 5 |
| 40 | 0.1 | 4 |
| 40 | 0.03 | 3 |
| 41 | 10 | 5 |
| 41 | 0.3 | 5 |
| 41 | 0.1 | 4 |
| 41 | 0.03 | 1 |
| 45 | 0.3 | 1 |
| 45 | 0.1 | 1 |
| 45 | 0.03 | 1 |
| 55 | 0.3 | 5 |
| 55 | 0.1 | 4 |
| 55 | 0.03 | 3 |
| 56 | 0.3 | 5 |
| 56 | 0.1 | 5 |
| 56 | 0.03 | 2 |
| 58 | 0.3 | 5 |
| 58 | 0.1 | 5 |
| 58 | 0.03 | 5 |
| 59 | 0.3 | 1 |
| 59 | 0.1 | 1 |
| 59 | 0.03 | 1 |
| 60 | 0.3 | 5 |
| 60 | 0.1 | 5 |
| 60 | 0.03 | 2 |
| 63 | 0.3 | 5 |
| 63 | 0.1 | 5 |
| 63 | 0.03 | 4 |
| 65 | 0.3 | 5 |
| 65 | 0.1 | 5 |
| 65 | 0.03 | 4 |
| 66 | 10 | 5 |
| 66 | 0.3 | 4 |
| 66 | 0.1 | 2 |
| 66 | 0.03 | 2 |
| 78 | 10 | 4 |
| 78 | 0.3 | 4 |
| 78 | 0.1 | 4 |
| 78 | 0.03 | 5 |
| 80 | 10 | 5 |
| 80 | 0.3 | 1 |

TABLE 2-continued

| Compound of Example No. | Concentration | Rating |
|---|---|---|
| 80 | 0.1 | 2 |
| 80 | 0.03 | 1 |
| 81 | 10 | 5 |
| 81 | 0.3 | 4 |
| 81 | 0.1 | 4 |
| 81 | 0.03 | 4 |
| 82 | 10 | 5 |
| 82 | 0.3 | 5 |
| 82 | 0.1 | 5 |
| 82 | 0.03 | 5 |
| 84 | 10 | 5 |
| 84 | 0.3 | 5 |
| 84 | 0.1 | 1 |
| 8.4 | 0.03 | 1 |
| 87 | 0.3 | 5 |
| 87 | 0.1 | 5 |
| 87 | 0.03 | 5 |
| 90 | 10 | 5 |
| 90 | 0.3 | 3 |
| 90 | 0.1 | 1 |
| 90 | 0.03 | 1 |
| 95 | 0.3 | 5 |
| 95 | 0.1 | 5 |
| 95 | 0.03 | 5 |
| 98 | 0.3 | 5 |
| 98 | 0.1 | 3 |
| 98 | 0.03 | 2 |
| 109 | 0.3 | 5 |
| 109 | 0.1 | 3 |
| 109 | 0.03 | 1 |
| 110 | 0.3 | 5 |
| 110 | 0.1 | 5 |
| 110 | 0.03 | 5 |
| 119 | 0.3 | 4 |
| 119 | 0.1 | 1 |
| 119 | 0.03 | 1 |
| 125 | 0.3 | 5 |
| 125 | 0.1 | 5 |
| 125 | 0.03 | 5 |
| 126 | 0.3 | 5 |
| 126 | 0.1 | 5 |
| 126 | 0.3 | 4 |
| 127 | 0.3 | 5 |
| 127 | 0.1 | 5 |
| 127 | 0.03 | 5 |
| 129 | 0.3 | 1 |
| 129 | 0.1 | 2 |
| 129 | 0.03 | 2 |
| 130 | 0.3 | 5 |
| 130 | 0.1 | 5 |
| 130 | 0.03 | 5 |
| 132 | 0.3 | 4 |
| 132 | 0.1 | 5 |
| 132 | 0.03 | 5 |
| 137 | 0.3 | 1 |
| 137 | 0.1 | 1 |
| 137 | 0.03 | 1 |
| 138 | 0.3 | 4 |
| 138 | 0.1 | 1 |
| 138 | 0.03 | 1 |
| 145 | 10 | 5 |
| 145 | 0.3 | 5 |
| 145 | 0.1 | 5 |
| 145 | 0.03 | 1 |
| 149 | 0.3 | 5 |
| 149 | 0.1 | 5 |
| 149 | 0.03 | 4 |

Test 4

Field Test Against Aquatic Weeds

Representative compounds were tested against typical aquatic weeds in artificial ponds maintained outdoors in full sunlight. The artificial ponds were plastic-lined cylindrical vessels, approximately 1 m. in diameter and 0.5 m. deep. A 10-cm. layer of soil was placed in the bottom of each pond, a 5-cm. layer of sand was added, and the ponds were filled with approximately 300 l. of water. The tests were conducted in the summer in the midwestern United States.

The weeds to be tested were allowed to become established in the ponds before treatment with the compounds. Those weeds which root in the hydro-soil were planted and allowed to become acclimated to the pond.

The compounds to be tested were formulated as described in Test 1, and were added to the ponds in adequate amounts to give the concentrations described in the table below, by diluting each portion of formulated compound in an amount of water equivalent to 50 gallons per surface acre, and spraying the aqueous dispersion over the surface of the pond.

After treatment with the compounds, the ponds were observed from time to time. Only the final observations are reported here, in terms of percent injury of the weeds. In the case of the weeds *Ceratophyllum demersum* and *Lemna minor*, the observation date was about 3 weeks after treatment. In the case of the other weeds, the observation date was approximately 12 weeks after treatment.

TABLE 3

| Compound of Example No. | Concentration | *Ceratophyllum demersum* | *Hydrilla verticillata* | *Lemna minor* | *Myriophylilum spicatum* | *Najas quadalupensis* | *Potamogen pectinatus* |
|---|---|---|---|---|---|---|---|
| 1 | 0.3 ppm | 100% | 100% | 100% | 100% | 100% | 100% |
| 1 | 0.1 | 95 | 50 | 85 | 100 | 95 | 90 |
| 1 | 0.03 | 95 | 0 | 85 | 100 | 100 | 100 |
| 29 | 0.3 | 100 | 100 | 99 | 100 | 100 | 100 |
| 29 | 0.1 | 100 | 100 | 90 | 100 | 100 | 100 |
| 29 | 0.03 | 100 | 98 | 50 | 100 | 100 | 110 |
| 72 | 0.3 | 85 | 50 | 70 | 50 | 50 | 50 |
| 72 | 0.1 | 100 | 100 | 100 | 100 | 100 | 100 |
| 72 | 0.03 | 100 | 48 | 60 | 100 | 100 | 100 |
| 87 | 0.3 | 100 | 35 | 99 | 100 | 100 | 100 |
| 87 | 0.1 | 85 | 0 | 75 | 75 | 48 | 0 |
| 87 | 0.03 | 45 | 0 | 0 | 50 | 0 | 0 |
| 105 | 0.3 | 85 | 50 | 65 | 50 | 50 | 50 |
| 105 | 0.1 | 50 | 0 | 30 | 0 | 0 | 0 |
| 105 | 0.03 | 25 | 0 | 0 | 0 | 0 | 0 |

Test 5

Field Test Against Aquatic Weeds

Another group of representative compounds were tested in artificial ponds outdoors according to the same test method used in Test 4 above. In these tests, the Lemna minor and Ceratophyllum demersum tests were observed about 4 weeks after treatment, and the other weeds were observed about 7 weeks after treatment.

TABLE 4

| Compound of Example No. | Concentration | Ceratophyllum Demersum | Hydrilla verticillata | Lemna minor | Myriophyllum spicatum | Najas quadalupensis | Potamogeton pectinatus |
|---|---|---|---|---|---|---|---|
| 1 | 0.3 ppm | 100% | 100% | 100% | 100% | 100% | 100% |
| 1 | 0.1 | 98 | 82 | 85 | 95 | 90 | 95 |
| 1 | 0.03 | 80 | 5 | 64 | 20 | 35 | 30 |
| 6 | 0.3 | 100 | 100 | 100 | 100 | 100 | 100 |
| 6 | 0.1 | 100 | 98 | 100 | 100 | 100 | 100 |
| 6 | 0.03 | 100 | 80 | 69 | 98 | 100 | 95 |
| 7 | 0.3 | 95 | 45 | 70 | 85 | 60 | 60 |
| 7 | 0.1 | 80 | 0 | 59 | 10 | 65 | 5 |
| 7 | 0.03 | 55 | 0 | 0 | 30 | 55 | 0 |
| 10 | 0.3 | 90 | 10 | 91 | 90 | 90 | 60 |
| 10 | 0.1 | 25 | 0 | 74 | 0 | 0 | 0 |
| 10 | 0.03 | 10 | 0 | 79 | 0 | 0 | 0 |
| 12 | 0.3 | 100 | 95 | 100 | 100 | 100 | 100 |
| 12 | 0.1 | 100 | 95 | 100 | 100 | 100 | 100 |
| 12 | 0.03 | 100 | 95 | 100 | 100 | 100 | 100 |
| 15 | 0.3 | 100 | 95 | 100 | 100 | 100 | 100 |
| 15 | 0.1 | 100 | 65 | 100 | 90 | 95 | 90 |
| 15 | 0.03 | 80 | 5 | 35 | 0 | 25 | 10 |
| 16 | 0.3 | 100 | 100 | 100 | 100 | 100 | 100 |
| 16 | 0.1 | 100 | 95 | 100 | 98 | 100 | 100 |
| 16 | 0.03 | 100 | 92 | 100 | 95 | 98 | 100 |
| 17 | 03 | 100 | 40 | 90 | 82 | 80 | 98 |
| 17 | 0.1 | 90 | 25 | 40 | 30 | 50 | 25 |
| 17 | 0.03 | 88 | 0 | 64 | 10 | 40 | 35 |
| 18 | 0.3 | 95 | 15 | 88 | 10 | 35 | 55 |
| 18 | 0.1 | 80 | 0 | 50 | 0 | 0 | 0 |
| 18 | 0.03 | 80 | 0 | 50 | 0 | 0 | 0 |
| 22 | 0.3 | 100 | 98 | 100 | 100 | 100 | 100 |
| 22 | 0.1 | 100 | 98 | 100 | 100 | 100 | 100 |
| 22 | 0.03 | 98 | 70 | 95 | 82 | 95 | 95 |
| 29 | 0.3 | 100 | 100 | 100 | 100 | 100 | 100 |
| 29 | 0.1 | 100 | 95 | 99 | 98 | 100 | 100 |
| 29 | 0.03 | 100 | 90 | 90 | 95 | 100 | 98 |
| 58 | 0.3 | 100 | 98 | 100 | 100 | 100 | 100 |
| 58 | 0.1 | 100 | 60 | 100 | 98 | 80 | 95 |
| 58 | 0.03 | 100 | 70 | 69 | 92 | 55 | 90 |
| 65 | 0.3 | 100 | 100 | 100 | 100 | 100 | 100 |
| 65 | 0.1 | 90 | 55 | 98 | 65 | 70 | 90 |
| 65 | 0.03 | 85 | 10 | 45 | 5 | 55 | 40 |

Test 6

Field Test Against Aquatic Weeds

The general method of Test 4 was used again in evaluating another group of representative compounds. The observation date was about 11 weeks after treatment in this group of tests.

TABLE 5

| Compound of Example No. | Concentration | Hydrilla verticillata | Myriophyllum spicatum | Najas flexilis | Potamogeton spectinatus |
|---|---|---|---|---|---|
| 1 | 0.3 ppm | 100% | 100% | 100% | 100% |
| 1 | 0.1 | 96 | 100 | 100 | 98 |
| 1 | 0.03 | 95 | 100 | 100 | 0 |
| 127 | 0.3 | 92 | 100 | 100 | 40 |
| 127 | 0.1 | 90 | 100 | 100 | 0 |
| 127 | 0.03 | 0 | 0 | 0 | 0 |
| 132 | 0.3 | 100 | 100 | 100 | 100 |
| 132 | 0.1 | 100 | 100 | 100 | 100 |
| 132 | 0.03 | 98 | 100 | 100 | 90 |

The broad-spectrum activity of the compounds used in this invention is clearly illustrated by the above examples. The compounds are effective against algae and aquatic weeds in general. For example, the following are typical aquatic weeds which are controlled by the compounds when applied at appropriate application rates: Cabomba caroliniana, Ceratophyllum demersum, Elodea canadensis, Hydrilla verticillata, Hydrochloa caroliniensis, Myriophyllum brasiliense, Myriophyllum spicatum, Najas guadalupensis, Nuphar advena, Panicum hemitomon, Panicum purpurascens, Panicum repens, Phalarsis arundinacea, Pontederia lanceolata, Potamogeton illinoensis, Sagittaria spp., Typha spp., Utricularia spp., and Vallisneria spp.

Further, the following genera of algae are exemplary of those controlled by the compounds when applied at suitable application rates: Amphora, Anabaena, Anacystis, Chlamydomonas, Chlorella, Cladophora, Cybella, Euglena, Diatoma, Rhizoclonium, Stichococcus, Scenedesmus, Volvox, Synura, Melosira, Nostoc, and Oscillatoria.

Most unusually, the compounds are herbicidally effective when applied both preemergence and postemergence. Thus, they can be applied to the water to kill weeds by contact when the weed seeds are germinating and emerging, and can also be used to kill emerged weeds by direct contact with the exposed portions of the weed. When the compounds are applied preemergence, the weeds are killed either during germination or shortly after emergence.

The compounds are effectively brought into contact with aquatic weeds and algae by either suspending or dissolving the compound in the water in which the weeds grow, or by applying the compound to the subaqueous soil in which the weeds are rooted.

The proportion of the weed population which is killed by an application of one of the compounds depends upon the species of the weed and the identity and amount of the compound applied. In many instances, of course, the whole population is killed. In other instances, part of the weeds are killed and part are injured, as some of the examples above illustrate. It will be understood that an application of one of the compounds is effective and beneficial, even though only part of the weed population is killed and another part of the population is injured. The term, "reducing the vigor of aquatic weeds or algae" is used generally herein to indicate the control produced by the compounds, whether the weeds or algae are killed or merely injured.

The best application rate of a given compound for the control of a given weed varies, of course, depending upon the method of compound application and climate and other factors known to those skilled in plant science. It will be found, however, that the optimum application rate is in the range of from about 0.1 to 20 kg./ha. in virtually every case. The optimum rates will usually be found to be within the preferred range of from about 0.1 to about 5 kg./ha.

Under some circumstances, it is preferred to measure the application rate by the concentration of the compound in the water. In particular, it is best to measure the application rate by concentration when the body of water is quite deep, or when the water is flowing or frequently disturbed by wind or thermal effects. Under such circumstances, concentrations from about 0.01 parts per million by weight (ppm) to about 15 ppm are effective. More preferably, rates from about 0.1 ppm to about 2 ppm are used.

The time when the compounds should be applied to the soil or the weeds is widely variable, since the compounds are effective both preemergence and postemergence. At least some control of the weeds will result from application of the compounds at any time when weeds are growing or germinating.

The compounds are applied in the manners usual in agriculture. They may be applied in the form of either water-dispersed or granular formulations, the preparation of which will be discussed below. The formulations are applied with any of the many types of sprayers and granular applicators which are in wide use for the distribution of agricultural chemicals.

Very often, the compounds are formulated as concentrated compositions which are applied in the form of water dispersions or emulsions containing in the range of from about 0.1 percent to about 5 percent of the compound. Water-dispersible or emulsifiable compositions are solids usually known as wettable powders, liquids usually known as emulsifiable concentrates, or suspensions. Wettable powders comprise an intimate, finely-divided mixture of the compound, an inert carrier and surfactants. The concentration of the compound is usually from about 10 percent to about 90 percent. The inert carrier is usually chosen from among the attapulgite clays, the kaolin clays, the montmorillonite clays, the diatomaceous earths or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates and nonionic surfactants such as ethylene oxide adducts of phenol.

Typical emulsifiable concentrates of the compounds comprise a convenient concentration of the compound, such as from about 10 to about 50 g. per liter of liquid, dissolved in an inert carrier which is a mixture of water-immiscible solvent and emulsifiers. Useful organic solvents include the aromatics, especially the xylenes, and the petroleum fractions, especially the high-boiling naphthalenic and olefinic portions of petroleum. Many other organic solvents may also be used such as the terpenic solvents, and the complex alcohols such as 2-ethoxyethanol. Suitable emulsifiers for emulsifiable concentrates are chosen from the same types of surfactants used for wettable powders.

Suspension compositions are convenient forms in which to use these compounds. Such compositions comprise the compound in finely powdered form suspended in a water-based liquid phase. The liquid phase usually comprises water, surfactants such as are used in wettable powders, an antifreeze such as propylene glycol, and a thickening agent, such as methyl cellulose, bentonite clay, or a vegetable gum. An anti-caking agent such as a fumed or precipitated silica may also be included. Suspensions are usually prepared by mixing the compound with the other ingredients, except the thickening agent, and grinding the mixture in a ball mill or similar device until the particles of compound are small enough to remain suspended. The thickener is then added. Usually suspensions contain amounts of compound in the range of 100 to 500 grams per liter.

A special type of emulsifiable concentrate composition is used to form invert emulsions. Such emulsions have the aqueous phase dispersed in the oil phase, and have been used for some years in the agricultural chemical industry. They are particularly useful in aquatic applications of the compounds, since they adhere very well to foliage, and do not rapidly disperse in water. Thus, by simple adjustment of the density, an invert emulsion can be accurately placed at the top or bottom of a body of water. Invert emulsion compositions usually include an inverting oil, a mixture of solvents and surfactants specially balanced to make invert emulsions when combined with water. See U.S. Pat. No. 3,197,229.

Another special type of composition which can be useful for application to water is one which forms a hydrophobic film. Such a composition, when applied to water, tends to spread itself evenly over the water surface, thereby achieving even application of the herbicide, despite any inaccuracy in applying the composition. Such compositions are usually based on a hydrophobic liquid, such as xylene, for example, in which the herbicide is dissolved or suspended.

Granular formulations are also particularly useful. Such formulations typically comprise the compound dispersed on a granular inert carrier such as coarsely ground clay. The particle size of granules usually ranges from about 0.1 to about 3 mm. The usual formulation process for granules comprises dissolving the compound in an inexpensive solvent and applying the solution to the carrier in an appropriate solids mixer. Somewhat less economically, the compound may be dispersed in a dough composed of damp clay or other inert carrier, which is then dried and coarsely ground to produce the desired granular product.

I claim:
1. A method of reducing the vigor of aquatic weeds or algae which comprises applying to water infested with or likely to be infested with such weeds or algae an herbicidally or algicidally effective amount of a compond of the formula

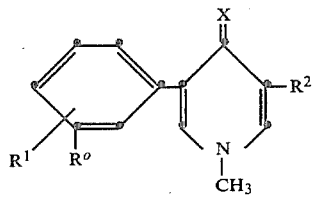

wherein
X represents oxygen or sulfur;
$R^o$ represents halo,
$C_1$-$C_4$ alkyl,
$C_1$-$C_4$ alkyl substituted with halo,
$C_1$-$C_4$ alkyl monosubstituted with phenyl, cyano or $C_1$-$C_3$ alkoxy,
$C_2$-$C_4$ alkenyl,
$C_3$-$C_6$ cycloalkyl,
$C_4$-$C_8$ cycloalkylalkyl,
$C_1$-$C_3$ alkanoyloxy,
phenyl,
nitro,
hydroxy,
$C_1$-$C_3$ alkoxycarbonyl,
—O—$R^3$,
—S—$R^3$, or
—SO—$R^3$;
$R^3$ represents $C_1$-$C_4$ alkyl,
$C_1$-$C_4$ alkyl substituted with halo,
$C_1$-$C_4$ alkyl monosubstituted with phenyl, cyano or $C_1$-$C_3$ alkoxy,
phenyl,
phenyl monosubstituted with halo, $C_1$-$C_3$ alkyl, $C_1$-$C_3$ alkoxy or nitro,
$C_3$-$C_6$ cycloalkyl,
$C_4$-$C_8$ cycloalkylalkyl, or
$C_2$-$C_4$ alkenyl;
$R^1$ represents halo,
hydrogen,
$C_1$-$C_4$ alkyl,
$C_1$-$C_4$ alkyl substituted with halo,
$C_1$-$C_4$ alkyl monosubstituted with phenyl, cyano or $C_1$-$C_3$ alkoxy,
methoxy, or
$C_2$-$C_4$ alkenyl;
$R^2$ represents hydrogen,
$C_1$-$C_3$ alkoxycarbonyl,
$C_1$-$C_6$ alkyl,
$C_1$-$C_6$ alkyl substituted with halo or $C_1$-$C_3$ alkoxy,
$C_2$-$C_6$ alkenyl,
$C_2$-$C_6$ alkenyl substituted with halo or $C_1$-$C_3$ alkoxy,
$C_3$-$C_6$ cycloalkyl,
$C_3$-$C_6$ cycloalkyl substituted with halo, $C_1$-$C_3$ alkyl or $C_1$-$C_3$ alkoxy,
$C_4$-$C_6$ cycloalkenyl,
$C_4$-$C_8$ cycloalkylalkyl,
phenyl-$C_1$-$C_3$ alkyl,
—O—$R^4$,
—S—$R^4$,
—SO—$R^4$; or

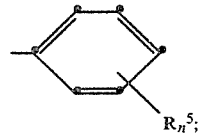

$R^4$ represents $C_1$-$C_3$ alkyl,
$C_1$-$C_3$ alkyl substituted with halo,
$C_2$-$C_3$ alkenyl,
$C_2$-$C_3$ alkenyl substituted with halo,
benzyl,
phenyl or
phenyl substituted with halo, $C_1$-$C_3$ alkyl or $C_1$-$C_3$ alkoxy;
the $R^5$ groups independently represent halo,
$C_1$-$C_4$ alkyl,
$C_1$-$C_4$ alkyl substituted with halo,
$C_1$-$C_4$ alkyl monosubstituted with phenyl, cyano or $C_1$-$C_3$ alkoxy,
$C_2$-$C_4$ alkenyl,
$C_3$-$C_6$ cycloalkyl,
$C_4$-$C_8$ cycloalkylalkyl,
$C_1$-$C_3$ alkanoyloxy,
hydroxy,
$C_1$-$C_3$ alkoxycarbonyl,
—O—$R^6$,
—S—$R^6$, or
—SO—$R^6$;
$R^6$ represents $C_1$-$C_4$ alkyl,
$C_1$-$C_4$ alkyl substituted with halo, or
$C_1$-$C_4$ alkyl monosubstituted with phenyl, cyano or $C_1$-$C_3$ alkoxy;
n represents 0–2;
and the acid addition salts thereof.

2. A method of claim 1 wherein the amount of the compound is from about 0.1 kg/ha to about 20 kg/ha.

3. A method of claim 2 wherein the vigor of aquatic weeds is reduced and the amount of the compound is from about 0.1 kg/ha to about 5 kg/ha.

4. A method of claim 1 wherein the amount of the compound is from about 0.01 parts per million by weight to about 15 parts per million by weight.

5. A method of claim 4 wherein the vigor of aquatic weeds is reduced and the amount of the compound is from about 0.1 parts per million by weight to about 2 parts per million by weight.

6. A method of claim 1, 2, 3, 4 or 5 wherein the compound is of the formula

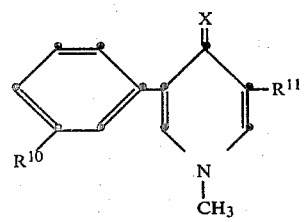

wherein X represents oxygen or sulfur;
$R^{10}$ represents trifluoromethyl, $C_1$-$C_3$ alkyl, halo, methoxy or methylthio;

$R^{11}$ represents $C_1$-$C_4$ alkyl, $C_1$-$C_3$ alkoxy, $C_1$-$C_3$ alkylthio, phenyl, phenoxy, phenylthio, or phenyl, phenoxyy or phenylthio monosubstituted with trifluoromethyl, $C_1$-$C_3$ alkyl, halo, methoxy or methylthio.

7. A method of claim 1, 2, 3, 4 or 5 wherein the compound is of the formula

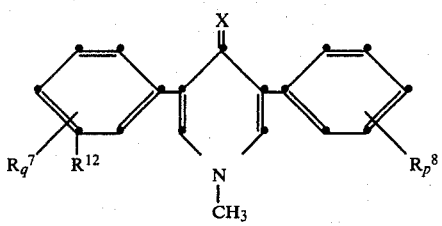

wherein
X represents oxygen or sulfur;
q represents 0-1;
p represents 0-2;
the $R^7$, $R^8$ and $R^{12}$ groups independently represent halo, $C_1$-$C_3$ alkyl, trifluoromethyl or $C_1$-$C_3$ alkoxy.

8. A method of claim 6 wherein the compound is a compound wherein X represents oxygen.

9. A method of claim 7 wherein the compound is a compound wherein X represents oxygen.

10. A method of claim 1, 2, 3, 4 or 5 wherein the compound is a compound wherein $R^1$ represents hydrogen, $R^0$ represents trifluoromethyl, and X represents oxygen.

11. A method of claim 1, 2, 3, 4 or 5 wherein the compound is 1-methyl-3-phenyl-5-(3-trifluoromethylphenyl)-4(1H)-pyridone.

12. A method of claim 1, 2, 3, 4 or 5 wherein the compound is 3-(3-fluorophenyl)-1-methyl-5-phenyl-4(1H)-pyridone.

13. A method of claim 1, 2, 3, 4 or 5 wherein the compound is 3-(3-chlorophenyl)-1-methyl-5-phenyl-4(1H)-pyridone.

14. A method of claim 1, 2, 3, 4 or 5 wherein the compound is 3,5-bis(3-chlorophenyl)-1-methyl-4(1H)-pyridone.

15. A method of claim 1, 2, 3, 4 or 5 wherein the compound is 3-(3-chlorophenyl)-5-(3-fluorophenyl)-1-methyl-4(1H)-pyridone.

16. A method of claim 1, 2, 3, 4 or 5 wherein the compound is 1-methyl-3-(3-methylphenyl)-5-phenyl-4(1H)-pyridone.

17. A method of claim 1, 2, 3, 4 or 5 wherein the compound is 3-(3-bromophenyl)-1-methyl-5-phenyl-4(1H)-pyridone.

18. A method of claim 1, 2, 3, 4 or 5 wherein the compound is 3-(3-methoxyphenyl)-1-methyl-5-phenyl-4(1H)-pyridone.

19. A method of claim 1, 2, 3, 4 or 5 wherein the compound is 3,5-bis(3-fluorophenyl)-1-methyl-4(1H)-pyridone.

20. A method of claim 1, 2, 3, 4 or 5 wherein the compound is 3-(2-chlorophenyl)-1-methyl-5-(3-trifluoromethylphenyl)-4(1H)-pyridone.

21. A method of claim 1, 2, 3, 4 or 5 wherein the compound is 3-(4-chlorophenyl)-1-methyl-5-(3-trifluoromethylphenyl)-4(1H)-pyridone.

22. A method of claim 1, 2, 3, 4 or 5 wherein the compound is 3-(2-fluorophenyl)-1-methyl-5-(3-trifluoromethylphenyl)-4(1H)-pyridone.

23. A method of claim 1, 2, 3, 4 or 5 wherein the compound is 3-(4-fluorophenyl)-1-methyl-5-(3-trifluoromethylphenyl)-4(1H)-pyridone.

24. A method of claim 1, 2, 3, 4 or 5 wherein the compound is 3-ethyl-1-methyl-5-(3-trifluoromethylphenyl)-4(1H)-pyridone.

25. A method of claim 1, 2, 3, 4 or 5 wherein the compound is 1-methyl-3-(3-methylthiophenyl)-5-phenyl-4(1H)-pyridone.

26. A method of claim 1, 2, 3, 4 or 5 wherein the compound is 3-(4-chloro-3-trifluoromethylphenyl)-1-methyl-5-phenyl-4(1H)-pyridone.

27. A method of claim 1, 2, 3, 4 or 5 wherein the compound is 3-(3-bromophenyl)-5-(3-chlorophenyl)-1-methyl-4(1H)-pyridone.

28. A method of claim 1, 2, 3, 4 or 5 wherein the compound is 3-(2-bromophenyl)-1-methyl-5-(3-trifluoromethylphenyl)-4(1H)-pyridone.

29. A method of claim 1, 2, 3, 4 or 5 wherein the compound is 1-methyl-3-(2-methylphenyl)-5-(3-trifluoromethylphenyl)-4(1H)-pyridone.

30. A method of claim 1, 2, 3, 4 or 5 wherein the compound is 3-(2-methoxyphenyl)-1-methyl-5-(3-trifluoromethylphenyl)-4(1H)-pyridone.

31. A method of claim 1, 2, 3, 4 or 5 wherein the compound is 3-(3-isobutylphenyl)-1-methyl-5-phenyl-4(1H)-pyridone.

32. A method of claim 1, 2, 3, 4 or 5 wherein the compound is 1-methyl-3-propyl-5-(3-trifluoromethylphenyl)-4(1H)-pyridone.

33. A method of claim 1, 2, 3, 4 or 5 wherein the compound is 3-ethoxy-1-methyl-5-(3-trifluoromethylphenyl)-4(1H)-pyridone.

34. A method of claim 1, 2, 3, 4 or 5 wherein the compound is 3-isopropoxy-1-methyl-5-(3-trifluoromethylphenyl)-4(1H)-pyridone.

35. A method of claim 1, 2, 3, 4 or 5 wherein the compound is 3-(4-chloro-3-trifluoromethylphenyl)-5-ethoxy-1-methyl-4(1H)-pyridone.

36. A method of claim 1, 2, 3, 4 or 5 wherein the compound is 1-methyl-3-(4-chloro-3-trifluoromethylphenyl)-5-propyl-4(1H)-pyridone.

37. A method of claim 1, 2, 3, 4 or 5 wherein the compound is 3-ethyl-1-methyl-5-(4-chloro-3-trifluoromethylphenyl)-4(1H)-pyridone.

38. A method of claim 1, 2, 3, 4 or 5 wherein the compound is 3-ethylthio-1-methyl-5-(3-trifluoromethylphenyl)-4(1H)-pyridone.

39. A method of claim 1, 2, 3, 4 or 5 wherein the compound is 1-methyl-3-propylthio-5-(3-trifluoromethylphenyl)-4(1H)-pyridone.

40. A method of claim 1, 2, 3, 4 or 5 wherein the compound is 1-methyl-3-isopropylthio-5-(3-trifluoromethylphenyl)-4(1H)-pyridone.

41. A method of claim 1, 2, 3, 4 or 5 wherein the compound is 1-methyl-3-(3-trifluoromethylphenyl)-5-trifluoromethylthio-4(1H)-pyridone.

42. A method of claim 1, 2, 3, 4 or 5 wherein the compound is 3-isopropyl-1-methyl-5-(3-trifluoromethylphenyl)-4(1H)-pyridone.

43. A method of claim 1, 2, 3, 4 or 5 wherein the compound is 3-(3,5-dichlorophenoxy)-1-methyl-5-(3-trifluoromethylphenyl)-4(1H)-pyridone.

44. A method of claim 1, 2, 3, 4 or 5 wherein the compound is 1-methyl-3-(2,2,2-trifluoroethoxy)-5-(3-trifluoromethylphenyl)-4(1H)-pyridone.

* * * * *

UNITED STATES PATENT AND TRADEMARK OFFICE
CERTIFICATE OF CORRECTION

PATENT NO. : 4,235,619
DATED : November 25, 1980
INVENTOR(S) : Harold M. Taylor

It is certified that error appears in the above-identified patent and that said Letters Patent are hereby corrected as shown below:

Column 6, line 55, "phenyl]-(3,5-" should read --phenyl]-5-(3,5- --.

Column 7, line 46, "3-(3-" should be at the beginning of line 47.

Column 13, line 20, that portion at the bottom of the formula that reads "$R^1$" should read -- $R^0$ --.

Column 19, line 25, "m.p. 113°" should read -- m.p. 133° --.

Column 30, line 17, "thylthylphenyl)" should read --thylphenyl)--

Column 36, across from Example No. 18, under "Concentration" should read -- 0.3 --, and under "Rating" should read -- 5 --. The next two lines, under Example No. 18, "65  0.003  4" and "66  5" should be deleted.

Column 37, line 15, "8.4" should read -- 84 --.

Column 37, line 38, across from the third Example No. 126 and under the heading "Concentration", "0.3" should read -- 0.03 --.

Column 39, in Table 4, across from the first Example No. 17, under the heading "Concentration", "03" should read -- 0.3 --.

Column 42, line 11, "10 to about 50 g." should read -- 100 to about 500 g. --.

UNITED STATES PATENT AND TRADEMARK OFFICE
CERTIFICATE OF CORRECTION

PATENT NO. : 4,235,619

DATED : November 25, 1980

INVENTOR(S) : Harold M. Taylor

It is certified that error appears in the above-identified patent and that said Letters Patent are hereby corrected as shown below:

Column 38, Table 3, column 6 of the table, the heading of the column "Myriophylilum" should read -- Myriophyllum --.
Column 8 of the table, the heading of the column "Potamogen" should read -- Potamogeton --.

Column 45, line 3, "phenoxyy" should read -- phenoxy --.

Signed and Sealed this

Twenty-first Day of July 1981

[SEAL]

Attest:

Attesting Officer

GERALD J. MOSSINGHOFF

Commissioner of Patents and Trademarks